United States Patent [19]
McDonell et al.

[11] Patent Number: 6,150,320
[45] Date of Patent: Nov. 21, 2000

[54] CONCENTRATED CLEANER COMPOSITIONS CAPABLE OF VISCOSITY INCREASE UPON DILUTION

[75] Inventors: James A. McDonell, Woodbury, Minn.; Jerry W. Mlinar, Hudson, Wis.

[73] Assignee: 3M Innovative Properties Company, St. Paul, Minn.

[21] Appl. No.: 08/928,789

[22] Filed: Sep. 12, 1997

Related U.S. Application Data

[63] Continuation of application No. 08/635,807, Apr. 22, 1996, abandoned, which is a continuation of application No. 08/278,514, Jul. 21, 1994, abandoned.

[51] Int. Cl.⁷ .............................. C11D 1/52; C11D 1/62; C11D 3/18; C11D 3/20
[52] U.S. Cl. ..................... 510/407; 510/138; 510/238; 510/365; 510/433; 510/437; 510/491; 510/501; 510/504
[58] Field of Search ..................... 510/407, 433, 510/437, 491, 500, 501, 503, 504, 505, 138, 365, 238

[56] References Cited

U.S. PATENT DOCUMENTS

| | | | |
|---|---|---|---|
| 2,710,843 | 6/1955 | Stebleton | 252/158 |
| 2,901,433 | 8/1959 | Spring | 252/118 |
| 2,929,789 | 3/1960 | Pickett et al. | 252/153 |
| 2,958,593 | 11/1960 | Hoover et al. | 51/295 |
| 3,202,714 | 8/1965 | Zimmerer et al. | 260/584 |
| 3,367,878 | 2/1968 | Mankowich | 252/110 |
| 3,463,735 | 8/1969 | Stonebraker et al. | 252/137 |
| 3,553,144 | 1/1971 | Murphy | 252/158 |
| 3,615,827 | 10/1971 | Murphy | 134/38 |
| 3,634,338 | 1/1972 | Laugle et al. | 252/525 |
| 3,664,962 | 5/1972 | Kelly et al. | 252/125 |
| 3,696,043 | 10/1972 | Labarge et al. | 252/153 |
| 3,806,460 | 4/1974 | Mukai et al. | 252/111 |
| 3,872,021 | 3/1975 | McKnight | 252/121 |
| 3,882,038 | 5/1975 | Clayton et al. | 252/164 |
| 3,892,669 | 7/1975 | Rapisarda et al. | 252/8.75 |
| 3,917,850 | 11/1975 | Boucher | 424/333 |
| 3,939,090 | 2/1976 | Zmoda | 252/90 |
| 3,943,234 | 3/1976 | Roggenkamp | 424/343 |
| 3,948,819 | 4/1976 | Wilde | 252/545 |
| 3,954,648 | 5/1976 | Belcak et al. | 252/158 |
| 4,013,607 | 3/1977 | Dwyer et al. | 260/29.6 H |
| 4,017,409 | 4/1977 | Demessemaekers et al. | 252/109 |
| 4,040,977 | 8/1977 | Eggensperger et al. | 252/401 |
| 4,140,648 | 2/1979 | Thompson et al. | 510/140 |
| 4,144,201 | 3/1979 | Wintebothan et al. | 252/547 |
| 4,174,304 | 11/1979 | Flanagan | 252/524 |
| 4,175,062 | 11/1979 | Disch et al. | 252/540 |
| 4,203,872 | 5/1980 | Flanagan | 252/542 |
| 4,225,471 | 9/1980 | Claus et al. | 252/547 |
| 4,235,734 | 11/1980 | Scherubel | 252/142 |
| 4,240,919 | 12/1980 | Chapman | 252/95 |
| 4,254,104 | 3/1981 | Suzuki | 424/170 |
| 4,264,466 | 4/1981 | Carleton et al. | 252/99 |
| 4,264,729 | 4/1981 | Beljanski | 435/6 |

(List continued on next page.)

FOREIGN PATENT DOCUMENTS

| | | |
|---|---|---|
| 0 129 980 | 1/1985 | European Pat. Off. . |
| 0 130 786 A3 | 1/1985 | European Pat. Off. . |
| 0 160 762 | 11/1985 | European Pat. Off. . |
| 0 314 232 | 5/1989 | European Pat. Off. . |
| 0314232 | 5/1989 | European Pat. Off. . |
| 0 518 401 A1 | 5/1992 | European Pat. Off. .......... C11D 1/83 |
| 0 595 590 A2 | 5/1994 | European Pat. Off. .......... C11D 1/83 |
| 0 666 303 | 8/1995 | European Pat. Off. . |
| 2 571 279 | 4/1986 | France . |
| 2 582 546 | 12/1986 | France . |
| 57-77111 | 6/1977 | Japan . |
| 54-14406 | 2/1979 | Japan . |
| 56-22397 | 3/1981 | Japan . |
| 57-28199 | 2/1982 | Japan . |
| 57-83598 | 5/1982 | Japan . |
| 58-185700 | 10/1983 | Japan . |
| 59-70652 | 4/1984 | Japan . |
| 40-76099 | 3/1992 | Japan . |
| 1 240 469 | 7/1971 | United Kingdom . |
| 1 602 234 | 11/1981 | United Kingdom . |
| 2 166 153 | 4/1986 | United Kingdom . |
| 2260771 | 4/1993 | United Kingdom . |
| WO 91/00337 | 1/1991 | WIPO . |
| WO 93/16162 | 8/1993 | WIPO . |
| WO 94/22996 | 10/1994 | WIPO . |
| WO 94/28108 | 12/1994 | WIPO . |

OTHER PUBLICATIONS

Hoffmann, H. et al., "The Different Phases and Their Macroscopic Properties in Ternary Surfactant Systems of Alkyldimethylamine Oxides, Intermediate Chain N–Alcohols and Water", Colloids Surf, vol. 67, pp. 223–237, 1992.

"Ethers for Household and Institutional Products", published 1976.

International Speciality Products product literature "Surfadone LP Speciality Solvents and Surfactants", 1992.

ARCO Chemical Company trade literature "Introducing ARCOSOLV PTB Solvent", 1991, pp. 2–5.

"Solvent Formulations From Eastman Chemicals", Sep. 1983.

Exxon Chemical Company product literature "AO–14–2", Dec. 4, 1991.

Exxon Chemical Company product literature "Non–Butyl Cleaners", Dec. 1980.

Exxon Chemical Company, "1992 Formulary", Mar. 8, 1989.

(List continued on next page.)

*Primary Examiner*—Lorna M. Douyon
*Attorney, Agent, or Firm*—Michaele A. Hakamaki

[57] ABSTRACT

Concentrated cleaning compositions are described which exhibit an increase in viscosity simply upon dilution with water. The concentrated and diluted ("ready-to-use") versions are useful in removing food and petroleum grease from hard surfaces (particularly non-horizontal surfaces), and may be formulated as petroleum degreasers, hand soaps and bathroom cleaners. The inventive compositions include an aggregate-forming organic compound, for example an amine oxide, and a nonaggregating or mildly aggregating organic compound, such as an organic alkyl alcohol having from about 4 to about 20 carbon atoms.

7 Claims, 6 Drawing Sheets

U.S. PATENT DOCUMENTS

| | | | |
|---|---|---|---|
| 4,297,251 | 10/1981 | Bernardino | 252/545 |
| 4,330,422 | 5/1982 | Tesch | 510/264 |
| 4,348,292 | 9/1982 | Ginn | 252/90 |
| 4,414,128 | 11/1983 | Goffinet | 252/111 |
| 4,460,374 | 7/1984 | Abel et al. | 8/501 |
| 4,501,680 | 2/1985 | Aszman et al. | 252/142 |
| 4,552,685 | 11/1985 | Kernstock et al. | 252/355 |
| 4,561,991 | 12/1985 | Herbots et al. | 252/118 |
| 4,576,728 | 3/1986 | Stoddart | 252/102 |
| 4,592,425 | 6/1986 | Oliver, Jr. et al. | 166/312 |
| 4,606,842 | 8/1986 | Keyes et al. | 252/174.23 |
| 4,606,850 | 8/1986 | Malik | 252/528 |
| 4,615,819 | 10/1986 | Leng et al. | 252/110 |
| 4,673,523 | 6/1987 | Smith et al. | 252/91 |
| 4,726,915 | 2/1988 | Verdicchio | 252/542 |
| 4,737,296 | 4/1988 | Watkins | 252/8.553 |
| 4,741,863 | 5/1988 | Yamamoto et al. | 252/547 |
| 4,749,509 | 6/1988 | Kacher | 252/139 |
| 4,758,377 | 7/1988 | Iding et al. | 252/556 |
| 4,767,563 | 8/1988 | Buzzaccarini | 252/174.25 |
| 4,769,172 | 9/1988 | Siklosi | 252/153 |
| 4,790,951 | 12/1988 | Frieser et al. | 252/162 |
| 4,814,108 | 3/1989 | Geke et al. | 252/545 |
| 4,814,109 | 3/1989 | Wittpenn, Jr. et al. | 252/547 |
| 4,863,629 | 9/1989 | Osberghaus et al. | 252/162 |
| 4,891,147 | 1/1990 | Gray et al. | 252/104 |
| 4,900,467 | 2/1990 | Smith | 252/90 |
| 4,909,962 | 3/1990 | Clark | 252/547 |
| 4,927,556 | 5/1990 | Pokoray | 252/173 |
| 4,948,520 | 8/1990 | Sasaki | 252/8.8 |
| 4,975,218 | 12/1990 | Rosser | 252/117 |
| 5,019,289 | 5/1991 | Gray et al. | 252/95 |
| 5,021,195 | 6/1991 | Machin et al. | 252/545 |
| 5,035,826 | 7/1991 | Durbut et al. | 252/121 |
| 5,041,239 | 8/1991 | Rorig et al. | 252/315.1 |
| 5,066,414 | 11/1991 | Chang | 252/8.8 |
| 5,080,822 | 1/1992 | VanEenam | 252/170 |
| 5,080,831 | 1/1992 | Van Eenam | 252/558 |
| 5,093,031 | 3/1992 | Login et al. | 252/257 |
| 5,106,613 | 4/1992 | Hartnett et al. | 424/71 |
| 5,126,068 | 6/1992 | Burke et al. | 252/174.21 |
| 5,130,046 | 7/1992 | Boulos et al. | 252/164 |
| 5,158,710 | 10/1992 | VanEenam | 252/539 |
| 5,252,245 | 10/1993 | Garabedian, Jr. et al. | 252/153 |
| 5,279,767 | 1/1994 | Phan et al. | 252/357 |
| 5,399,285 | 3/1995 | Kanluen | 252/174.23 |
| 5,460,736 | 10/1995 | Trinh et al. | 252/8.8 |
| 5,462,689 | 10/1995 | Choy et al. | 252/90 |
| 5,573,710 | 11/1996 | McDonell | 510/405 |
| 5,643,865 | 7/1997 | Mermelstein et al. | 510/521 |
| 5,674,832 | 10/1997 | Keys | 510/504 |

OTHER PUBLICATIONS

"Household and Personal Products Industry", May 1982, pp. 48–54.

Chemical Abstracts, vol. 94 (1981) Jun., No. 26, Columbus, OH p. 110.

"Eastman, Solvent Selector Chart" Trade Literature of Eastman Chemical Products, Inc., U.S., Feb. 1987, p. 2.

"Amine Oxides and Their Applications" Rorig and Stephan, La Rivista Italiana Delle Sostanze Grasse, vol. LXVII, Guiogno 1991.

"Cationic Surfactants As Thickening Agents In Hard Surface Cleansers," AKZO Presentation in Toronto 1992 (Paper Presumably Published or to be Published in JAOCS Later).

"Cationic Surfactants in Cleaner Formulations," Stephan, Tenside Surf. Det. 29(1992)3.

"Take 5 Industrial Cleaning System" Brochure, 1 page, Trade Literature, U.S., 1991.

Chemron Corporation Material Safety Data, dated Jan. 6, 1994.

Operating Instructions–Bostwick Consistometer, CSC Scientific Company, Inc. undated.

Ethyl Corporation–Chemicals Group, Materials Safety Data Sheets (6), dated Sep. 2, 1993.

World Poultry Article "Gel Cleaning–Effective Across The Food Chain", Misset, vol. 9, No. 11, 1993, pp. 17–18.

Database WPI, Week 8719, Derwent Publications Ltd., London, GB; AN 87–129789 & DD,A,242053 (Veb Leuna–Werk Ulbright), Jan. 14, 1987.

Database WPI, Week 7909, Derwent Publications Ltd., London, GB: AN 79–16823B & JP,A,54008607 (KANEBO) Jan. 23, 1979.

Database WPI, Week 8703, Derwent Publications Ltd., London, GB; AN 87–017887 & JP,A,61 275 398 (KAO Corp.) Dec. 5, 1986.

Database WPI, Week 8703, Derwent Publications Ltd., London, GB, AN 87–0178866 & JP,A,61 275 397 (KAO Corp.) Dec. 5, 1986.

Database WPI, Week 9147, Derwent Publications Ltd., London, GB AN 91–344786 & JP,A,03,232,000 (CCI), Oct. 15, 1991.

CONCENTRATED CLEANER COMPOSITIONS CAPABLE OF VISCOSITY INCREASE UPON DILUTION

This is a continuation of application Ser. No. 08/635,807 filed Apr. 22, 1996 now abandoned, which is a continuation of application Ser. No. 08/278,514 filed Jul. 21, 1994 now abandoned.

BACKGROUND OF THE INVENTION

1. Brief Description of the Invention

The present invention relates to concentrated cleaning compositions in general, and in particular compositions formulated as petroleum degreasers, hand soaps and bathroom cleaners, which may be increased in viscosity upon dilution with water without the use of desolubilizer compounds.

2. Related Art

In assignee's copending application Ser. No. 08/039,632, filed March 30, 1993, entitled "Multi-Surface Cleaning Compositions and Method of Use", now abandoned, which was continued as Ser. No. 08/327,481 filed Oct. 21, 1994 now abandoned, which was continued as Ser. No. 08/587,246 filed Jan. 16, 1996, now U.S. Pat. No. 5,573,710, there is disclosed and claimed cleaning compositions which will effectively remove greasy residues while not leaving significant streaks on a hard surface, and which preferably can be used on surfaces other than hard surfaces, such as carpet, furniture, and the like. The '632 application focuses on the surprising discovery that specific compounds having surfactant function, particularly amine oxides and quaternary amine salts, when combined with a very slightly water-soluble polar organic compound, had a surprising synergistic effect in removal of grease. In addition when a third ingredient, comprising an effective amount of a water-soluble glycol ether or alcohol, was added, the compositions were substantially non-streaking on hard surfaces. Further, the compositions were useful in removing food residues from carpet and upholstery, and are thus termed "non-streaking multi-surface" cleaning compositions.

In certain cleaning applications, it is desired to formulate premix concentrates which are relatively non-viscous for ease of packaging and dispensing, but which are capable of "thickening" (substantially increasing in viscosity) over a large range of water dilutions when ready to use. For example, users frequently desire to clean non-horizontal surfaces, such as walls, and do not wish the cleaner to run off prematurely.

There have been disclosed various additives which allow thickening of cationic surfactant compositions such as those described in the '632 application. Colloidal compounds, such as colloidal magnesium aluminum silicate, may be used for such purposes, as well as various polysaccharides. Various electrolytes, such as sodium chloride, will also allow thickening. Cationic surfactant compositions themselves exhibit an increase in viscosity as the concentration of cationic surfactant increases. At high concentrations (typically greater than 20 weight percent, sometimes greater than 50 weight percent) the shape of micelles changes from spherical to rod shape. The high concentrations of cationic surfactant required to achieve this, however, are impractical in ready to use cleaner formulations. To address this problem, additive compounds typically described as "desolubilizers" may be added which shift the viscosity-increase toward lower concentrations of surfactant. Desolubilizers are typically organic anionic sulfonates, such as cumene, xylene, and toluene sulfonates, in their acid or salt forms, and certain hydrophobically modified polymer surfactants.

With the technical advances in proportioners and other mechanical liquid dispensing systems, it would be an advance in the art to have cleaning concentrates which are low viscosity, easily pumpable or easily gravity feedable, which, when diluted, form a viscous ready-to-use composition which, for example, will readily cling to non-horizontal surfaces.

SUMMARY OF THE INVENTION

In accordance with the present invention, concentrated cleaner compositions are described which exhibit an increase in viscosity simply upon dilution with water, without the addition of desolubilizers or additional surfactants, such as nonionic and anionic surfactants or hydrophobically modified polymers. The concentrated and diluted ("ready-to-use") versions are useful in removing grease, marks, and the like from hard surfaces (particularly non-horizontal surfaces), and may be formulated into petroleum degreasers, hand soaps and bath cleaners.

The inventive compositions comprise:

A) an aggregate-forming organic compound (a compound capable of forming lamellar or micellar aggregates in aqueous solution), and B) a nonaggregating or mildly aggregating organic compound (preferably an amphiphilic organic compound, a compound having both a polar, water-soluble moiety, and a hydrophobic, water insoluble moiety), the aggregate-forming organic compound and the nonaggregating organic compound present in a weight ratio sufficient to afford a composition which is phase-stable, substantially homogeneous, has a viscosity of less than 1 second BC, and is readily mixable with water without significant energy input to form a ready-to-use ("RTU") composition. The RTU composition has a viscosity of at least 5 seconds BC at weight ratios of water to the composition of 8:1 and greater.

"BC" refers to a viscosity measured using a "Bostwick Consistometer", using a test method as further described in the Test Methods section. All BC viscometer measurements herein refer to the time in seconds for the test fluid to traverse 20 cm of a horizontal flow trough at 20° C. A viscosity of 1 second BC is about 100 centipoise as measured using a Brookfield viscometer, spindle #1, at 60 rpm, 20° C., or about 50 seconds using a Zahn viscometer, #1 cup. A value of 300 seconds BC is about 10,000 centipoise or greater using the above-mentioned Brookfield viscometer.

In the compositions of the invention, (i) the aggregate-forming organic compound is selected from the group consisting of amine oxides, quaternary amine salts, and noncyclic alkanolamides; and (ii) the nonaggregating organic compound is selected from the group consisting of
  a) very slightly water-soluble organic compounds selected from the group consisting of alcohols, N-alkyl cyclic amides, and organic acids, and
  b) mineral oils, with the provisos that if the aggregate-forming organic compound is (a) an amine oxide, then the nonaggregating organic compound is either an alcohol, an N-alkyl cyclic amide, or combination thereof;

(b) a quaternary amine salt, then the nonaggregating organic compound is either an alcohol, an organic acid, or combination thereof;

(c) a noncyclic alkanolamide, then the nonaggregating organic compound is either an N-alkyl cyclic amide, an amine, a mineral oil, or combination thereof.

It was surprising that specific combinations of aggregate-forming organic compounds, particularly amine oxides and quaternary amine salts, when combined with a very slightly water-soluble nonaggregating or mildly aggregating organic compound, were capable of being thickened over large water dilution ranges and exhibited excellent grease removal.

Concentrates of the invention having initial viscosity of about 1 second BC may have their viscosity increased at least to 5 seconds BC, preferably to 5 to 300 seconds BC, at dilution factors greater than 8:1. "Dilution factor", as used herein means the weight of water per weight of concentrate.

As used herein the term "very slightly water-soluble" denotes a class of nonaggregating or mildly aggregating organic compounds useful in the invention which are soluble in water at concentrations ranging from about 0.01 to about 1.0 weight percent at 20° C., more preferably from about 0.01 to 0.05 weight percent. Mineral oils are substantially water insoluble. "Hard surface" is meant to include surfaces such as glass window panes, ceramic tiles, marble, terrazzo, and the like. The term "fibrous substrate" is meant to include relatively porous materials such as carpet, upholstery, clothing, and the like, and is meant to exclude hard surfaces such as glass, ceramic tile, and the like.

Amine oxide aggregate-forming organic compounds useful in the invention for use in combination with very slightly water-soluble nonaggregating organic alcohols and N-alkyl cyclic amides include compounds selected from the group consisting of amine oxides within the general formula (I)

$$R^1R^2R^3N \rightarrow O \tag{I}$$

wherein $R^1$ and $R^2$ are the same or different and are selected from the group consisting of alkyl and substituted alkyl groups, $R^3$ is selected from the group consisting of straight chain alkyls, branched chain alkyls, straight chain heteroalkyls, and branched chain heteroalkyls, each having from about 10 to 20 carbon atoms. An example within formula (I) is dimethylmyristylamine oxide. Compositions of the invention employing branched chain alkyl ether amine oxides as the aggregate-forming organic compound produce less foam than the same composition using a n-alkyl or other straight-chain ether amine oxide. This may be advantageous when easy rinsing of the compositions of the invention from the substrate to be cleaned is desired. Of course, in some instances it may be desired to employ an n-alkyl amine oxide when foaming of the composition is desired, for example in hand soaps.

Quaternary amine salts useful as aggregate-forming organic compounds in conjunction with amphiphilic alcohols and organic acids include quaternary amine salts within the general formula (II):

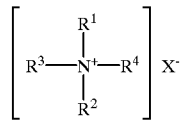

wherein $R^1$, $R^2$, and $R^3$ are as above described for the amine oxides, $R^4$ is selected from the group consisting of alkyl groups having from 1 to about 5 carbon atoms (preferably methyl), and X is a halogen atom, preferably atomic chlorine. One preferred quaternary amine salt is isodecyloxypropyldihydroxyethylmethyl ammonium chloride.

Noncyclic alkanolamides useful as aggregate-forming organic compounds in conjunction with N-alkyl cyclic amides and amines include compounds selected from the group consisting of alkanolamides within general formula (III):

wherein $R^5$ and $R^6$ are the same or different and are selected from the group consisting of hydroxyalkyl groups having from about 2 to 4 carbon atoms, and n ranges from 4 to 20. An example of a useful alkanolamide within general formula (III) are the mixed fatty acid alkanolamides known under the trade designation MONAMID 150 ADY.

Examples of very slightly water-soluble nonaggregating organic amphiphilic compounds useful in the compositions of the invention include straight chain and branched chain organic alkyl alcohols having from 4 to about 20 carbon atoms, such as 1-hexanol, isooctyl alcohol, 1-octanol, 2-ethyl hexanol, and 1-decanol, and other organic alcohols having from 4 to 20 carbon atoms; straight chain and branched chain tertiary and secondary alkyl amines having from 4 to about 20 carbon atoms; N-alkyl cyclic amides such as N-alkyl pyrrolidones wherein the alkyl group has from about 8 to about 20 carbon atoms, such as N-octyl pyrrolidone and the like; organic acids having from about 4 to about 20 carbon atoms, such as octanoic, pelargonic (nonanoic), and lauric (dodecanoic) acids. Surprisingly, although not truly amphiphilic compounds, in certain compositions, mineral oils have been found to function as amphiphiles, for example toward non-cyclic alkanolamides.

All but the N-alkyl cyclic amides are nonaggregating, while the N-alkyl cyclic amides are mildly aggregating amphiphiles.

Optional water-soluble glycol ethers may be included in the compositions since they are useful for their ability to decrease the viscosity of concentrate compositions of the invention. In this usage, "water-soluble" means having a water solubility at 20° C. of greater than 10 weight percent, more preferably infinite water solubility. These include propylene glycol mono-t-butyl ether (water solubility of about 16 weight percent) and propylene glycol mono-methyl ether, which is infinitely soluble in water.

If the nonaggregating or mildly aggregating organic compound is an N-alkyl cyclic amide or an organic acid, optional water-soluble alkyl alcohols and/or glycol ethers may be included for their ability to decrease viscosity of the concentrated compositions of the invention. Examples of suitable water-soluble alcohols include propanol, isopropanol, butanol, isobutanol and the like, with isopropanol being particularly preferred. Propylene glycol methyl ether is a preferred water-soluble glycol ether.

Various optional (active and/or inactive) ingredients may be included in all versions of the inventive compositions. As used herein the term "active" means the ingredient alone or in combination has an effect on the cleaning, thickening and/or non-streaking ability of the composition. In contrast, "inactive" means the component is added primarily for aesthetic purposes, such as odor, color, and the like. The aggregate-forming organic compounds and the nonaggregating organic compounds described herein are considered actives. The concentrated compositions of the invention may include inactive ingredients such as water, thinning agents, fragrances, and dyes, and actives such as pH adjustment ingredients (for example low molecular weight hydroxy-functional amines), chelating agents, and the like, as long as the concentrate viscosity does not exceed 1 second BC, and as long as they do not interfere with phase stability, ability to increase in viscosity upon dilution with water, and the like.

The concentrated compositions of the invention may be dispensed by any one of a number of methods, including pumping (mechanical or "hand" pump), gravity feed, proportioner, venturi, and other dispensing means, as further discussed herein.

Further aspects of the invention are methods of cleaning soiled hard surfaces, fibrous substrates, and "natural" surfaces such as human skin. The methods comprise diluting a cleaning-effective amount of concentrate of the invention with water using a low-shear dispensing device to form an RTU composition having the desired viscosity, applying the RTU composition to the soiled surface, and removing the soil and RTU composition from the hard surface or fibrous substrate, as the case might be. As used herein the term "soiled hard surface" means a hard surface that has a residue such as food grease, petroleum grease, heel marks and the like thereon. When substances such as pencil, pen, permanent marker and china marker lines or marks are to be removed, the method preferably further comprises scrubbing the soiled hard surface with an abrasive article, preferably a nonwoven abrasive such as that described and claimed in U.S. Pat. No. 2,958,593 (Hoover et. al.).

Further aspects and advantages of the invention will become apparent by reviewing the drawing, description of preferred embodiments and examples which follow.

DESCRIPTION OF PREFERRED EMBODIMENTS

Figure 1:
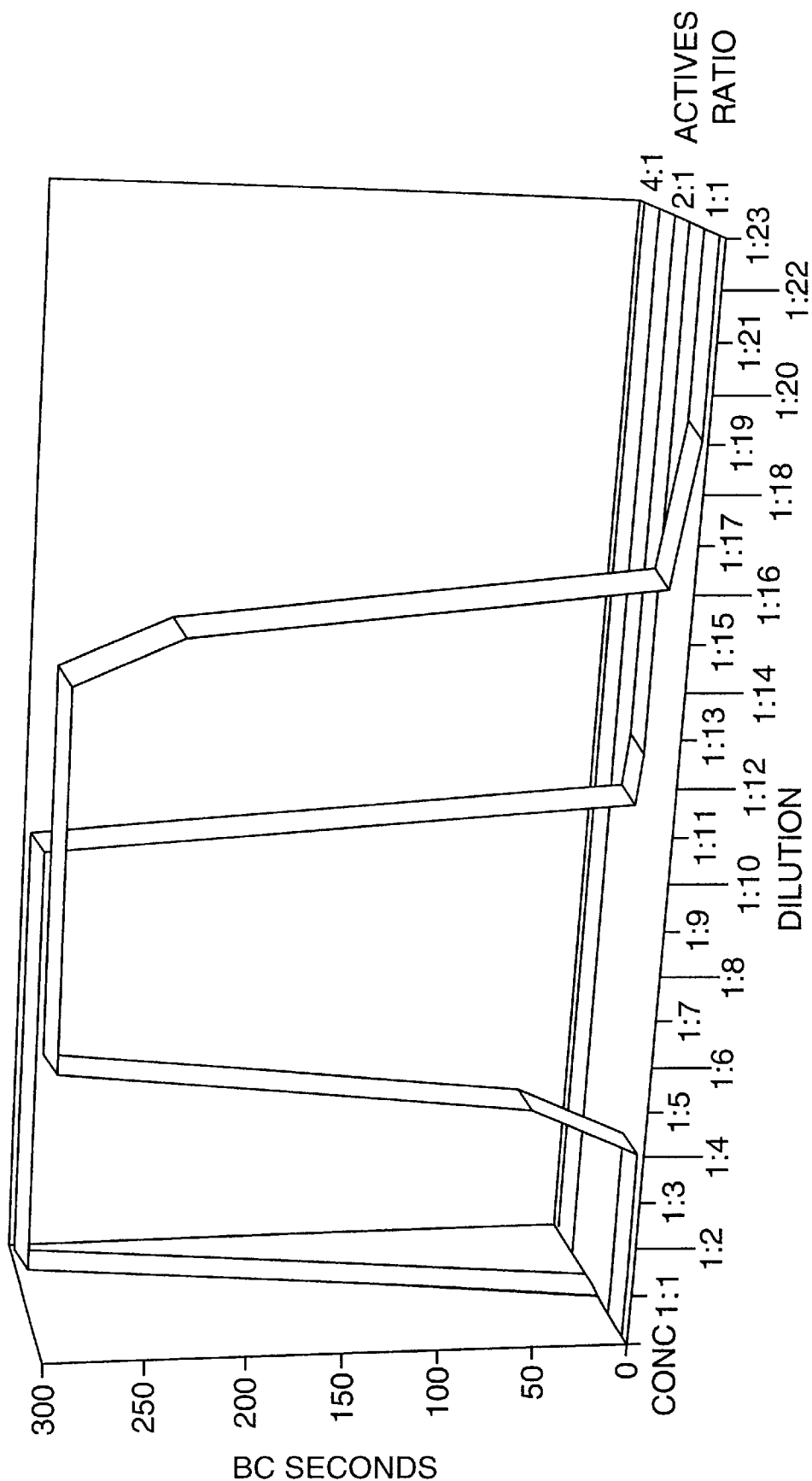
FIGS. 1–6 are three-dimensional graphical representations of viscosity increase upon dilution of compositions within the invention, in particular the compositions of Examples 3, 4, 37, 46, 50 and 73.

In order that the present invention may be more fully understood, a digression into the state of the art is deemed useful.

A convenient method of analyzing the formation of aggregates such as "normal" micelles, "inverse micelles", and "lamellar liquid crystals" in a conventional ternary system of octanoic acid, water and sodium octanoate is by using the following equation:

$$R = V_H / a_0 l$$

wherein:

$V_H$ is the volume of the hydrophobic portion of the aggregate;

$a_0$ is the cross-sectional area of the hydrophilic portion of the aggregate;

l is the is the length of the hydrophilic portion of the aggregate; and

R is a qualitative value whose magnitude depends on the shape of the aggregates, wherein:

| R value | aggregate shape |
|---|---|
| R < 1/3 | sphere (normal micelle) |
| 1/3 < R < 1/2 | cylinder |
| 1/2 < R < 1 | lamellar |
| R > 1 | sphere (inverse micelle). |

Thus, a normal micelle in the water, octanoic acid, sodium octanoate ternary system occurs at very low amounts of octanoic acid (an oil-in-water system), with the hydrophobic portions of the octanoic acid inside the spherical micelles. As the ratio of octanoic acid to water increases, the octanoic acid acts as a desolubilizer, changing the shape of the aggregates from normal spheres (less viscous) to lamellar liquid crystals, with an attendant increase in system viscosity. Finally, as the ratio of octanoic acid to water increases to the point where the system becomes a water-in-oil system, the shape of the micelles change back to spherical, but the micelles are inversed (hydrophobic portion of the octanoic acid molecules form the external surface of the micelles), with an attendant decrease in viscosity.

The concentrated cleaning compositions of the present invention have been carefully formulated to be capable of being increased in viscosity above 1 second BC simply by diluting with water. The combinations of aggregate-forming organic compound and nonaggregating organic components of the present invention allow the user to easily control the viscosity of the RTU versions.

In addition, the combinations of aggregate-forming organic compound and nonaggregating organic components of the present invention are effective (in RTU form) in removing grease and other soils from hard surfaces. The individual components of the concentrated cleaning compositions of the invention will now be described in greater detail.

I. Aggregate-Forming organic compounds

A. Amine Oxides

Amine oxides useful in the cleaning compositions of the invention which have been found to have excellent cleaning and thickening ability in the presence of very slightly water-soluble alcohol and N-alkyl cyclic amide amphiphiles include amine oxides such as the amine oxide/polyethylene glycol mixture known under the trade designation "ADMOX LA-1440", available from Albemarle Chemical Co., Baton Rouge, La., in which the amine oxide of the mixture is characterized by $R^1$ and $R^2$ each being methyl, while $R^3$ is myristyl, this amine oxide also known as N,N-dimethyl-1-tetradecamine oxide dihydrate. The polyethylene glycol (PEG) portion of the mixture has a molecular weight of about 200, having 4 ethylene oxide units, although the molecular weight may range anywhere from 100 to 300. These amine oxide/PEG mixtures are high foaming, make their use especially attractive in handsoaps. Another useful amine oxide within general formula I is that wherein $R^1$ and $R^2$ are each methyl, and $R^3$ is $C_{12}$ alkyl, such as lauryldimethylamine oxide. Yet another useful amine oxide is lauramidopropyl-N,N-dimethylamine oxide.

Procedures for making tertiary amine oxides of the type useful in the invention are well known. Tertiary amines are oxidized cleanly to tertiary amine oxides, a procedure known as the Cope Reaction (see Streitwieser, Jr. et al. *Introduction to Organic Chemistry*, pp. 793–794 (Macmillan Publishing Co., Inc. 1976). Useful oxidants are $H_2O_2$ or organic peroxyacids of the formula $RCO_3H$. Other methods of making tertiary amine oxides, including mixtures containing branched chain and straight chain $R_3$ groups, are explained in U.S. Pat. No. 4,576,728, at columns 2–3, which is incorporated by reference herein. Such mixtures are suitable for use in the present invention. Secondary amines oxides may also prove useful, although their use is less desirable from the standpoint of commercial availability.

B. Quaternary Amine Salts

Quaternary amine salts are based on the reaction of high molecular weight aliphatic tertiary amines with an alkylating agent such as methyl chloride. They are generally more cationic and more stable to pH change than other amine-based aggregate-forming organic compounds, such as ethoxylated amines. Quaternary amine salts useful as aggregate-forming organic compounds in the cleaning compositions of the invention which have excellent cleaning and thickening effect in combination with very slightly water-soluble alcohol and organic acid amphiphiles include those within general formula II in which $R^1$ and $R^2$ are each hydroxyethyl, and $R^3$ is isotridecyloxypropyl. Two particularly preferred quaternary amine salts include the one known under the trade designation "Q-17-2", from Tomah Chemical, Milton, Wis., wherein $R^1$ and $R^2$ are each hydroxyethyl, and $R^3$ is isotridecyloxypropyl, $R^4$ is methyl, and X is atomic chlorine, and the quaternary amine salt known under the trade designation "Q-14-2 PG", also available from Tomah Chemical, wherein $R^1$ and $R^2$ are each hydroxyethyl, and $R^3$ is isodecyloxypropyl, $R^4$ is methyl, and X is atomic chlorine.

C. Noncyclic Alkanolamides

Noncyclic alkanolamides within general formula III useful as aggregate-forming organic compounds in the cleaning compositions of the invention which have excellent cleaning and thickening effect with very slightly water-soluble N-alkyl cyclic amides and amine amphiphiles include 1:1 lauric diethanolamide, 1:1 coconut diethanolamide, 1:1 mixed fatty acid diethanolamide, coconut diethanolamide, "modified", 1:1 soya diethanolamidopoly(ethyleneoxy) ethanol, and coconut diethanolamide, "long chain modified". Methods of production of noncyclic alkanolamides useful in the invention are well known in the chemical arts and no further explanation is deemed necessary.

It should be appreciated that a combination of aggregate-forming organic compounds within general formulas I, II and III may be employed in the compositions of the invention, provided the selected compounds within general formulas I, II and III are compatible with each other and the other active and inactive ingredients, or capable of being rendered compatible therewith, and provided they produce the desired thickening and cleaning effects in conjunction with the selected nonaggregating organic compound component upon dilution of the whole with water.

II. Nonaggregating Organic compounds

One class of nonaggregating or mildly aggregating organic compounds useful in the invention in promoting the formation of aggregates of the aggregate-forming organic compound are very slightly water-soluble organic amphiphile compounds. Another class of useful nonaggregating or mildly aggregating organic compounds are the water insoluble mineral oils.

Any one of a number of very slightly water-soluble organic compounds may be used in the compositions of the invention, with the following provisos:

1) they have the ability to remove grease, food soils, and the like from hard surfaces and/or human skin;

2) provided they have a water solubility less than about 1.0 weight percent, more preferably less than about 0.5 weight percent, but in all cases more than 0.01 weight percent (all water solubilities referred to herein are at 20° C.); and 3) provided they form a phase-stable concentrate with the aggregate-forming organic compound having a viscosity less than 1 second BC, and at least at some ratios of aggregate-forming organic compound to very slightly water-soluble organic compound the concentrate may be thickened upon dilution with water to a viscosity of 5 seconds BC or greater.

Mixtures of very slightly water-soluble organic compounds, and mixtures of very slightly water-soluble compounds with mineral oils may be used, provided they are sufficiently compatible with each other and with the other active and inactive ingredients.

A. Organic Acids

One class of preferred nonaggregating, very slightly water-soluble, amphiphilic organic compounds for use in promoting aggregates of quaternary amine salts are organic acids having from about 4 to about 20 carbon atoms, such as octanoic, pelargonic (nonanoic), decanoic and lauric (dodecanoic) acids. One preferred commercially available organic acid meeting these requirements is octanoic acid, available under the trade designation EMERY 659, from Emery Industries, Cincinnati, Ohio, a subsidiary of Henkel Corporation.

B. Alcohols

Another class of useful very slightly water-soluble, aggregate-promoting, amphiphilic organic compounds useful in the present invention include straight and branched chain alkyl alcohols having from about 4 to about 20 carbon atoms, such as isooctyl alcohol (water solubility of 0.06 weight percent), 1-octanol, and 2-ethyl hexanol (each having a water solubility of about 0.1 weight percent). Isooctyl alcohol is available under the trade designation "Exxal 8" from Exxon Chemical Company, Houston, Tex. According to Exxon Chemical Company trade literature, "Exxal 8" is a mixture of isomers, the major isomers being dimethyl-1-hexanol and methyl-1-heptanol.

Other useful very slightly water-soluble, aggregate-promoting, amphiphilic organic alcohols include alkylene glycol alkylethers, such as ethylene glycol mono-2-ethylhexylether, available under the trade designation EKTASOLVE EEH, from Eastman Chemicals, Kingsport, Tenn.

C. Cyclic N-alkyl Amides

Yet another class of very slightly water soluble, aggregate-promoting, amphiphilic organic compounds useful in the present invention are cyclic N-alkyl amides, such as N-alkyl pyrrolidones, having water solubility within the preferred ranges previously mentioned, and as described generally in U.S. Pat. No. 5,093,031, incorporated herein by reference. These compounds can be mildly aggregate forming, as explained in the '031 patent. One useful example is N-octyl pyrrolidone (solubility of 0.124 weight percent in water), available under the trade designation "Surfadone LP-100" from International Specialty Products, Wayne, N.J. It should be noted that although the N-alkyl pyrrolidones are themselves very slightly water-soluble, the addition of a small quantity of an anionic or a non-ionic surfactant may increase their solubility and wetting speed.

D. Fatty Amines

Saturated and unsaturated fatty amines may be used in the compositions of the invention, with unsaturated fatty amines being preferred due to their generally lower viscosity.

Fatty amines found useful as very slightly water-soluble, aggregate-promoting, amphiphilic organic compounds include fatty amidoamines within the general formula (IV)

(IV)

wherein $R_7$ and $R_8$ are the same or different straight chain or branch chain alkyl groups having from 1 to 6 carbon atoms, $R_9$ is a straight chain alkyl group having from 2 to 6 carbon atoms, and Rio is a straight chain or branch chain alkyl group having from 10 to 30 carbon atoms.

Useful fatty amidoamines include the following saturated amidoamines:
dimethylcocoamidopropylamine
dimethyloleylamidopropylamine,
dimethylhexadecanamidopropylamine,
dimethyloleylamidoethylamine,
dimethylhexadecanamidoethylamine, and the like.

Dimethyloleylamidopropylamine is available under the trade designation "CHEMIDEX O", from Chemron Corporation, Paso Robles, Calif.

Useful unsaturated amidoamines include dimethyl stearylamidopropylamine and dimethyl lineoleylamidopropylamine.

Other useful fatty amines include those within formula (IV) above, but with the amido group $-C(=O)R^{10}$ replaced with hydrogen, such as dimethylcocoamine, dimethyloctylamine, and the like.

E. Mineral Oils

Mineral oils are also useful nonaggregating organic compounds when employed with non-cyclic alkanolamides as the aggregate-forming organic compound. Useful mineral oils have the following properties: viscosity of 7 to 10 centistokes at 40° C., and 50 to 60 Saybolt Seconds Universal at 37.8° C., specific gravity (25° C.) ranging from about 0.82 to about 0.85, pour point ranging from about 0 to about −10C, and flash point ranging from about 130 to 150° C. One mineral oil within this description is the light mineral oil known under the trade designation "KLEAROL", from Witco Chemical Co., which has specific gravity (25° C.) ranging from about 0.827 to about 0.838, pour point of −7° C., and flash point of 138° C.

III. Ratio of Active Ingredients

In compositions in accordance with the invention, the weight ratio of active aggregate-forming organic compound to nonaggregating organic compound typically and preferably ranges from about 1:5 to about 5:1, more preferably from about 1:1 to about 5:1.

In particular, for combinations of amine oxide with an amphiphile, it is preferred that the weight ratio of active amine oxide to active amphiphile range from about 1:1 to about 5:1, at dilution factors ranging from 1:1 to 18:1, more preferably ranging from 1:1 to 2:1. For combinations of quaternary amine salt and amphiphile, it is preferred that the weight ratio of active quaternary amine salt to active amphiphile range from about 1:1 to about 5:1, more preferably ranging from 1:1 to 2:1, at dilution factors ranging from 1:1 to 16:1. For combinations of noncyclic alkanolamide with either an amphiphile or a mineral oil, it is preferred that the weight ratio of active noncyclic alkanolamide to active nonaggregating organic compound range from about 1:1 to about 6:1, at dilution factors ranging from 1:1 to 16:1.

In the examples which follow, it is evident that not all combinations of an aggregate-forming organic compound with a nonaggregating organic compound exhibit the ability to increase in viscosity when diluted with water. Examples of nonaggregating organic compounds commonly used in hard surface cleaning compositions but which proved unsuitable in combination with the aggregate-forming compound known under the trade designation "ADMOX LA-1440" include mineral oils, and the very slightly water-soluble organic amphiphile compounds hexyl acetate, lauric acid, octanoic acid, pelargonic acid, diisobutylcarbinol, and N-octyl pyrrolidone. The nonionic organic compound known under the trade designation "ALFONIC810-40" (a 100% $C_8$–$C_{10}$ alcohol ethoxylate) and the amphoteric surfactant known under the trade designation "MIRATAINE JC-HA" did not aggregate using any of the very slightly water-soluble organic amphiphilic compounds commonly used in hard surface cleaning compositions. However, the noncyclic alkanolamide known under the trade designation "MONAMID 150ADY" (a mixed fatty acid alkanolamide) formed aggregates well in conjunction with N-alkyl pyrrolidones, mineral oils, and fatty amines, but not with alkyl alcohols, alkyl acetates, organic acids, and diisobutylcarbinol. The aggregate-forming organic compound known under the trade designation "Q-14-2 PG" did not readily form aggregates with N-alkyl pyrrolidones, mineral oils, fatty amines, alkyl acetates, or diisobutylcarbinol. The anionic surfactant known under trade designation "WITCOLATE ES370" (%70 sodium lauryl ether sulfate, three ethoxylate groups) formed aggregates only with cyclic N-alkyl amides having alkyl group of 12 or more and with alkyl alcohols.

IV. Optional Ingredients

The compositions of the present invention may include various optional additives such as a colorant to provide a more aesthetic appearance, a fragrance to provide more acceptable smell, a preservative to prevent microbial growth in the solution, a suitable agent to eradicate germs, mold, mildew, antioxidants, chelating agents which may be required with certain other surfactants, pH adjustment chemicals other than the acid component, and the like. Such components are well known in the art and specific amounts of each will be within the knowledge of the skilled artisan. One preferred fragrance is citronellol, which may also provide amphiphilic thickening.

If deionized water is not to be used as the dilution medium, it is frequently desired to add a chelating agent to the concentrate, such as 1-hydroxyethylidene-1, 1-diphosphonic acid. This chelating agent is available under the trade designation "Dequest" 2010, from Monsanto Corporation, St. Louis, Mo. This component is typically added to the concentrate at a weight percent ranging from about 0.1 to about 0.3 weight percent.

Suitable antioxidants include butylated hydroxytoluene ("BHT"), available from Exxon Chemical Company, Houston, Tex. Antioxidants prevent or reduce the formation of peroxides, which may catalyze the degradation of the dye or other ingredients.

Acids found useful for adjusting viscosity of the inventive compounds include acetic, formic, and gluconic acids, and the like. This component functions primarily to optimize the thickening upon dilution, and secondarily to decrease pH, and therefore may not be required in all formulations. The preferred pH for hand soaps ranges from about 3 to 9, while for degreasing compositions the pH is preferably 6 or greater. The nonaggregate-promoting acid component actually employed usually depends on considerations such as mildness to skin, corrosiveness, and similar properties. The nonaggregate-promoting acid component is typically present in compositions of the invention, with the weight ratios of aggregate forming organic compound to acid ranging from about 20:1 to about 30:1.

Water-soluble glycol ethers may be useful in the compositions of the invention for reducing viscosity. These include ethylene glycol methyl ether, ethylene glycol ethyl ether, ethylene glycol mono-n-butyl ether, diethylene glycol methyl ether, diethylene glycol ethyl ether, methoxy triglycol, ethoxy triglycol, butoxy triglycol, 1-butoxyethoxy-2-propanol, propylene glycol n-propyl ether, propylene glycol methyl ether, dipropylene glycol methyl ether, 3-methyl-3-methoxybutanol, propylene glycol mono-t-butyl ether, and the like and combinations thereof. A particularly preferred glycol ether is propylene glycol monomethyl ether, available under the trade designations "Dowanol" PM (from Dow Chemical Company, Midland, Mich.), "Propasol Solvent M" (from Union Carbide Corporation, Danbury, Connecticut), and "Arcosolv" PM (from Arco Chemical Company, Philadelphia, Pa.).

Preferred water soluble alkyl alcohols for fine tuning of viscosity were previously mentioned. One preferred water soluble alkyl alcohol is isopropanol.

The weight ratio of active aggregate-forming organic compound within general formulas I, II and III to optional active viscosity-reducing water-soluble glycol ether or alkyl alcohol preferably ranges from about 1:1 to about 20:1.

V. Dispensing Methods for the Inventive Compositions

The concentrated compositions of the invention may be dispensed by any one of a variety of means. Various mechanical dispensing devices may be utilized, all preferably of the low energy mixing variety. By "low energy" is meant that the concentrate does not require significant energy input or specialized mechanical equipment to effect viscosity increase upon dilution with water as it leaves the dispensing container.

A. Gravity Feed Dispensers

An example of a preferred dispenser is the gravity feed dispenser disclosed in assignee's pending patent application Ser. No. 08/050,529, now U.S. Pat. No. 5,425,404 filed Apr. 20, 1993, incorporated by reference herein. Disclosed therein is a system for dispensing a fluid, including a bottle having a cavity for receiving a quantity of the fluid and an orifice communicating between the cavity and exteriorly of the bottle. A valve is mounted on the bottle about the orifice for controlling flow of the fluid. The valve is shiftable between a first, closed position preventing flow of the fluid from the bottle, and a second, open position for dispensing the fluid from the bottle through the orifice at a predetermined rate.

Although the dispensing system of the '529 invention might employ any suitable bottle or other container for the concentrate, in the preferred embodiment of the invention, the bottle is constructed according to co-pending U.S. patent application Ser. No. 08/049,844, also filed Apr. 20, 1993, now U.S. Pat. No. 5,435,451 entitled "Bottle for Fluid Dispensing System", and commonly assigned to the assignee of the present invention, the contents of which are incorporated herein by reference. Means may be provided as part of the bottle to resist "paneling". Paneling occurs with the bottle inverted and as the fluid level is reduced. A partial vacuum is created in the "headspace" above the level of the liquid within the bottle. The walls of the bottle are gradually deflected inwardly under the influence of the partial vacuum. This deflection acts to retard the flow of the fluid from the bottle. The deflection increases until a point is reached where a quantity of the liquid is rapidly dispensed from the bottle and the walls quickly flex outwardly, whereby the pressure in the head space is equalized with the ambient pressure. The fluctuation of the flow of fluid from the bottle due to paneling prevents accurate metering of the dispensing of the fluid or dilution of the fluid. By "resist", it is meant that paneling is reduced or eliminated when the bottle is inverted and the fluid is being dispensed. One paneling control means includes a shoulder separating upper portions of the first and second sides of the bottle from a pair of parallel, laterally spaced external gripping surfaces. The shoulder, or any like sharp change in the shape or geometric configuration of the bottle acts to strengthen the sides of the bottle to resist paneling.

A dispenser assembly is included for supporting the bottle while dispensing the fluid. The dispenser includes a body having a dilution chamber, a receiving opening and a dispensing opening below the receiving opening, each communicating with the dilution chamber. Supporting means are provided for engaging and supporting the bottle on the body with the orifice of the bottle directed downwardly through the receiving opening, wherein when the valve is in the open position the fluid is dispensed from the bottle and outwardly from the dispenser assembly through the dispensing opening. Means are provided for shifting the valve on the bottle from the closed position to the open position to enable dispensing of the fluid, the shifting means being actuated when the bottle is engaged with the supporting means.

Means are provided for connection to a source of a diluting fluid (typically tap water, preferably deionized water) and for conveying the diluting fluid to the diluting chamber. A diluting valve is provided for controlling the flow of the diluting fluid into the dilution chamber. The diluting valve is shiftable between an open position enabling flow of the diluting fluid into the dilution chamber, and a closed position preventing flow of the diluting fluid into the dilution chamber, with the diluting valve being biased to the closed position. Switch means are provided for shifting the diluting valve to the open position responsive to the bottle being received by and engaged with the supporting means of the dispenser body, to enable the diluting fluid to flow into the diluting chamber, whereby the fluid from the bottle and the diluting fluid will intermix in the diluting chamber and flow outwardly of the dispenser assembly though the dispensing opening.

The '529 application further discloses a dispenser assembly for use with a bottle containing a quantity of a fluid to be dispensed, with a valve cap for controlling the flow of the fluid from the bottle.

B. Non-Gravity Feed Dispensers

Other dispensing techniques may be utilized, such two chamber sprayers or simply pouring from a container. One known two chamber sprayer is that known under the trade designation TAKE 5, available from Rollout LP, Anaheim, Calif. Spraying can be accomplished by conventional mechanical spraying devices (such as by use of a conventional trigger spray device) or by using an aerosol dispensing container having a sufficient amount of suitable aerosol propellant. Suitable aerosol propellants are those such as low boiling alkanes or mixtures thereof, such as a mixture isobutane and propane, as is known in the art.

Other useful, preferred systems have been developed in the past for dispensing fluids in a controlled manner. Such systems have included positive displacement systems in which a fluid is suctioned from a container, such as by a pump. For instance, the "Compublend" brand cleaning chemical management system available from the Minnesota Mining and Manufacturing Company Co. of St. Paul, Minn. is an example of one such system. While having its own utility, positive displacement systems generally are expensive and complicated, and may not be desirable for relatively low volume applications.

Another acceptable approach is to utilize a venturi effect to suction a fluid from a container. As is known in the art, the velocity of the water creates a lower pressure in the stream that induces the fluid to be siphoned into the stream, simultaneously diluting the fluid. An example of a venturi effect fluid dispensing system is the Hydro Omni-Clean brand proportioning and dispensing system available from the Hydro Systems Company of Cincinnati, Ohio.

However, venturi effect fluid dispensing systems, while having their own utility, are undesirable for many situations in which high levels of accuracy and consistency are desired or required. Typically, conventional venturi effect systems provide an accuracy rate that widely varies from the desired rate. That is, over time, although average rates may be close to what is desired, fluctuations in the flow rate may widely exceed or fall below desired values.

Other acceptable dilution methods include conventional metering, for example using the bottle known under the trade designation ACCUMIX, from S.C. Johnson & Son, Racine, Wis., wherein a bottle has a head space adapted to accumulate a prescribed amount of the concentrate after the bottle has been inverted. Another convenient low energy mixing method is a pouch, typically made of plastic or metal, in which the concentrated cleaning composition is mixed with water.

VI. Methods of Use of the Inventive Compositions

After applying the compositions of the invention to the surface to be cleaned, the compositions may simply be wiped away with the food or other soil by using a nonabrasive, preferably absorbent material, or the surface may be scrubbed with an abrasive or nonabrasive article, such as a lofty, open, three-dimensional nonwoven abrasive article as described by Hoover et. al. in U.S. Pat. No. 2,958,593, incorporated herein by reference, and then wiped dry with a non-abrasive material.

A further understanding of the ability to thicken the concentrate compositions of the invention and the use of ready-to-use versions in removing food grease and petroleum grease from hard surfaces will be understood with reference to the following Examples and Test Methods. In the Examples which follow all parts and percentages are by weight unless otherwise specified.

Test Methods

Bostwick Consistometer Viscosity Testing Method

This test utilized a viscometer consisting of a trough divided into two sections by a gate. The smaller section serves as a reservoir for the material to be tested. The larger section is graduated along the bottom in one-half centimeter divisions beginning at the gate. The gate is spring-operated and is held by a trigger that permits instantaneous release. In operation, the gate slides vertically in the grooves of two posts extending upward from the sides of the trough. The L-shaped trigger release hooks over the top of the gate to hold it in a closed position. Two leveling screws are located at the reservoir end of the trough and a circular spirit level is located at the other end of the trough.

Before testing the compositions of the following Examples, the consistometer was placed on a level surface and the leveling screws adjusted until the bubble in the circular level was centered. The level was checked by placing another spirit level on the bottom of the trough about midway along the length of the graduated section. The gate was closed and the trigger release hooked over the top. Each composition tested was prepared by holding it at a constant temperature after water dilution (room temperature of about 20° C.) for about ½ hour to assure a uniform temperature sample.

For each composition tested, the reservoir was filled with the composition to be tested and leveled off with a spatula. The trigger release was pressed down and simultaneously a stop watch started. The time for the composition to reach 5, 10, and 20 centimeters down the trough was recorded. The maximum reading was taken at the center of the trough and the minimum taken at one edge, and the values averaged.

Hard Surface Cleaning Tests

Some of the ready-to-use compositions within the invention were tested using two tests: food grease removal and petroleum grease removal.

Test Method 1: Food Grease Removal Test

In the food grease removal tests, a standard food grease solution consisting of equal amounts of soy bean oil and lard dissolved in enough methylene chloride to form a solution was prepared. A small amount of oil blue pigment was added to the solution. 25 millimeter (mm)×75 mm glass slides were then immersed for a few seconds into the food grease and drawn up quickly so that the food grease coated both sides of the slide (25 mm×30 mm on each side). The food grease-coated slides were then dried or "cured" by hanging at room temperature (about 20° C.) for 24 hours.

In the food grease removal test, 140 milliliters (ml) of composition to be tested were placed into a 150 ml glass beaker equipped with a magnetic stir bar (2.5 cm in length). The beaker was then placed on a magnetic stirrer (Barnant Co. model no. 700-5011). The coated glass slide to be cleaned was then suspended vertically in the composition to be tested, coated portion pointing toward the bottom of the beaker with the other end attached to a suitable support, so that the glass slide did not touch anything but the composition being tested, and the stir bar did not hit the glass slide or the sides of the beaker. The magnetic stirrer was immediately turned on and the stirring speed adjusted with a strobe light to 2000 rpm, after which the percent removal of food grease versus time was measured visually for each side of the slide. Slides were not reused.

Test Method 2: Petroleum Grease Removal Test

This test was similar to the food grease removal test. A standard petroleum grease was prepared (at least 2–7 days prior to testing) consisting of 25 grams 20 weight oil, 25 grams industrial lithium grease known under the trade designation "STA-Grease" from Conoco Oil Company, 75 grams heptane, 75 grams methylene chloride and 0.2 gram oil soluble dye. These ingredients were mixed in a beaker equipped with a stir bar and placed on a heater/magnetic stirrer and the grease heated to about 30° C. while keeping a watch glass over the beaker. After the composition reached about 30° C. the beaker was removed from the heater/magnetic stirrer and allowed to cool to room temperature with continued stirring with a glass rod. 25 mm×75 mm glass slides were then immersed for a few seconds into the petroleum grease and drawn up quickly so that the grease coated both sides of the slide (25 mm×30 mm on each side). The food grease-coated slides were then dried by hanging at room temperature (about 20° C.) for 24 hours.

In the petroleum grease removal test, 140 ml of composition to be tested was placed into a 150 ml glass beaker equipped with a magnetic stir bar (2.5 cm in length). The beaker was then placed on a magnetic stirrer (Barnant Co. model no. 700-5011) and the power setting adjusted until the bar rotated at 2000 rpm, using a strobe light to adjust the speed of rotation. The coated glass slide to be cleaned was then suspended vertically in the composition to be tested, coated portion pointing toward the bottom of the beaker with the other end attached to a suitable support, so that the glass slide did not touch anything but the composition being tested, and the stir bar did not hit the glass slide or the sides of the beaker. The percent removal of the petroleum grease was measured visually versus time for each slide and composition tested. Slides were not reused.

Reproducibility for the grease removal Test Methods 1 and 2 is about +/−5%.

Materials Description

The following materials were used in the Examples which follow:

| | |
|---|---|
| "Q-14-2 PG" | is the trade designation for a quaternary amine salt surfactant available from Tomah Chemical Co., Milton, Wisconsin, and is a mixture of 50 weight percent isotridecyloxypropyl dihydroxyethyl methyl ammonium chloride, 50 weight percent propylene glycol; |
| "WITCOLATE ES-370" | is the trade designation for an anionic which is 70 weight percent sodium lauryl ether sulfate, from Witco Chemical Company; |
| "ADMOX LA-1440" | is the trade designation for a 40 weight percent solution of dimethylmyristyl amine oxide, available from Albemarle Chemical Co., Baton Rouge, Louisiana; |
| "MIRATAINE JC-HA" | is the trade designation for an aqueous solution of an alkyliminopropionate amphoteric aggregate-forming organic chemical, available from Rhone-Poulenc, Cranberry, New Jersey; |

EXAMPLES

Examples 1–72

Viscosity Testing

Table 1 lists the combinations of aggregate-forming organic chemicals ("AFOC") with very slightly water-soluble organic amphiphile compounds tested for their ability to increase in viscosity when diluted with water. For each combination of aggregate-forming organic chemical and very slightly water-soluble organic amphiphile compound, three "dilution numbers" (weight ratio of active aggregate-forming organic chemical to active very slightly water-soluble organic amphiphile compound) were prepared, 1:1, 2:1 and 4:1, as detailed in Table 2. These were then diluted manually in a beaker by weight with deionized water at various "concentrations" as set out in Table 2, from 1:1 up to 1:24. The numbers filling in the rows of Table 2 are the BC viscosity values (having units of seconds) using the Bostwick Consistometer Viscosity Testing Method, described above. In Table 2, "N/S" means "not soluble".

Drawing Figures

For the purposes of viewing the drawing figures, note that the highest value for BC seconds shown in the drawings (300 seconds BC) does not mean that the composition tested had that value, but that it simply would have taken longer than 300 seconds for the composition to run the entire 20 cm course of the trough of the viscometer.

Figure 2:
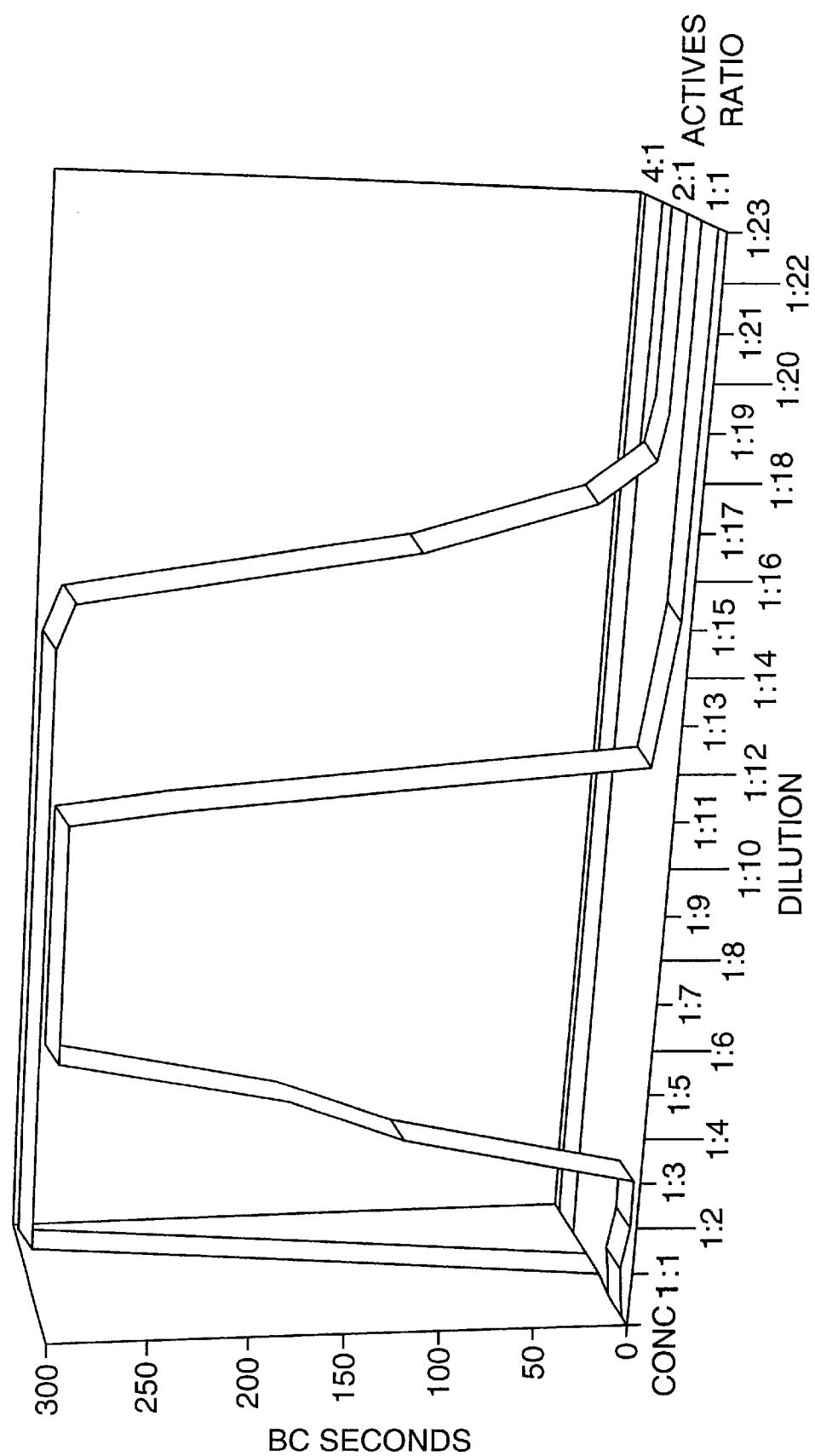
Figure 3:
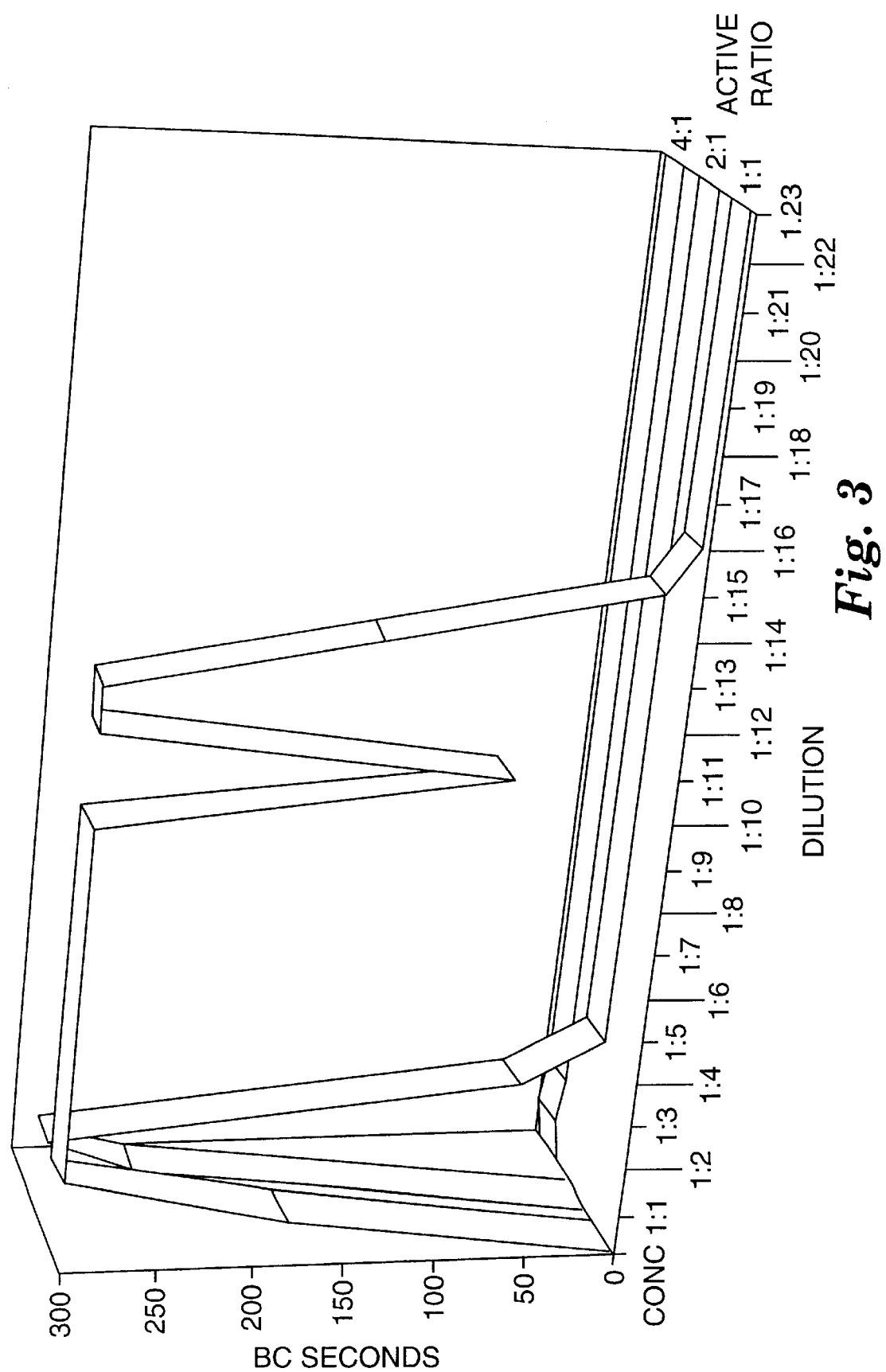
Figure 4:
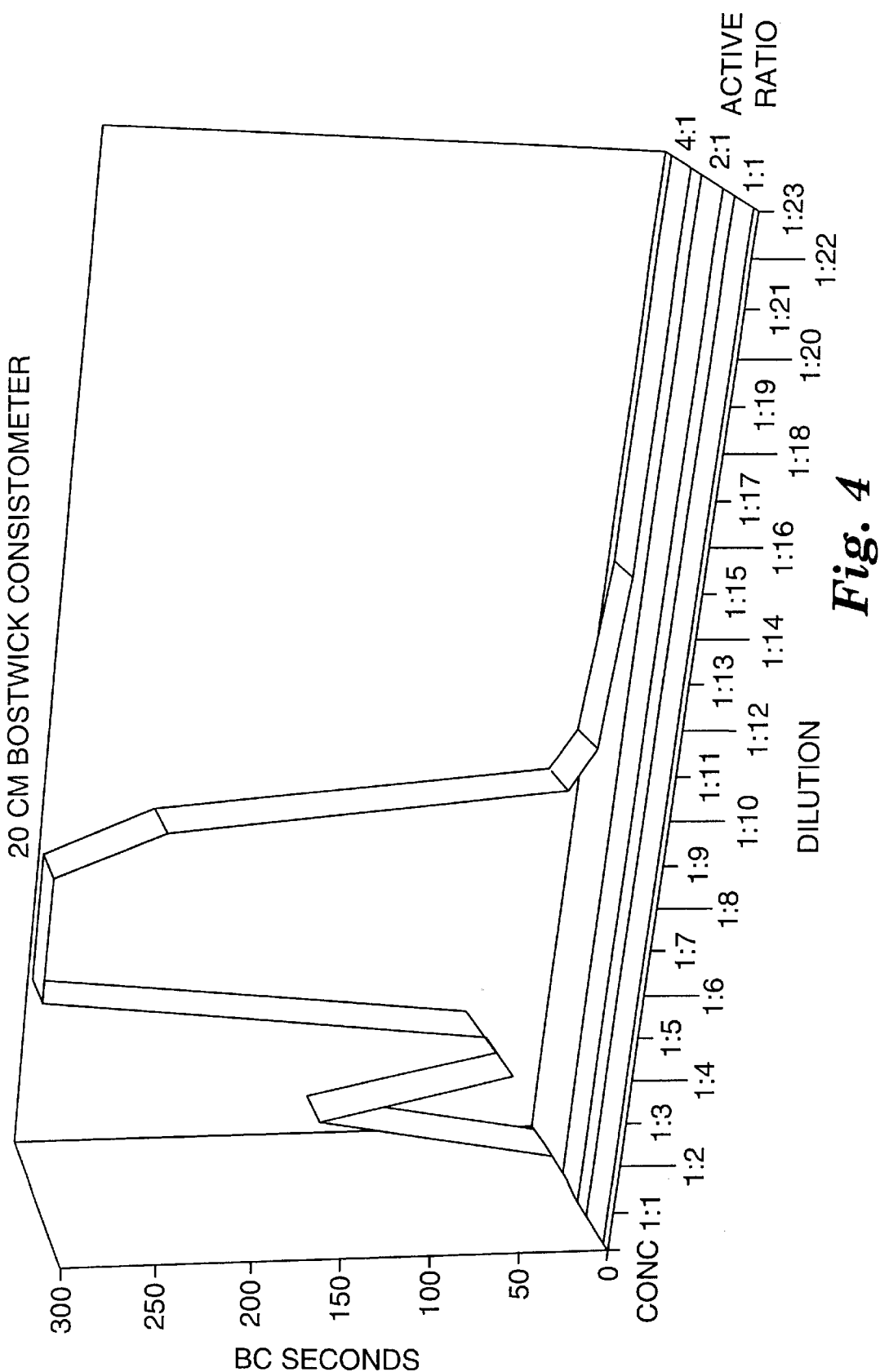
Figure 5:
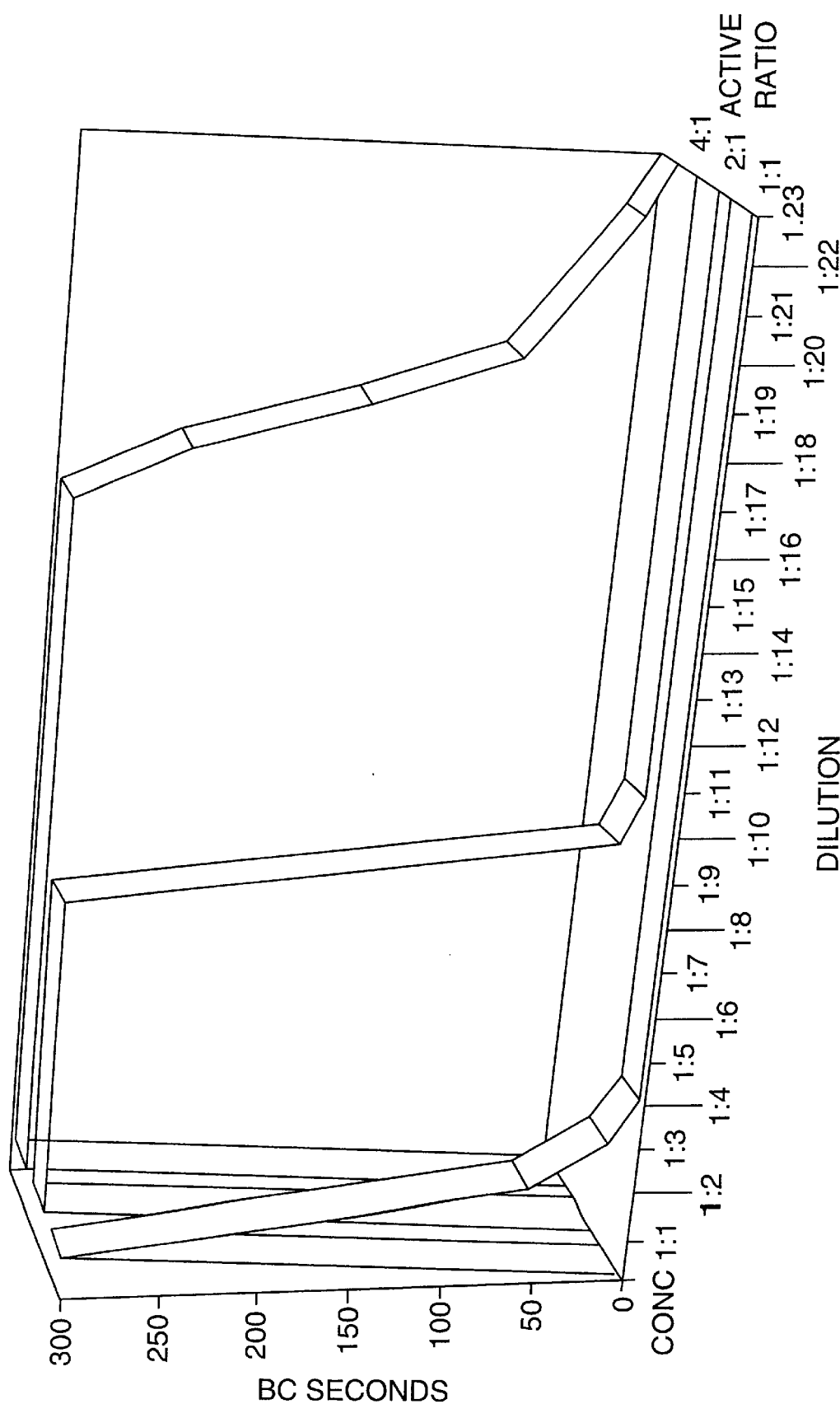

As can be seen by viewing the drawing figures, FIGS. 1 and 2 illustrate that the compositions of Examples 3 and 4 (amine oxide with an alkanol) exhibited significant thickening upon dilution at the 1:1 and 2:1 actives ratios, with little or no thickening at the 4:1 actives ratio. FIG. 3 illustrates that the composition of Example 37 (quaternary amine salt/octanol) exhibited thickening at higher water dilution ratios when the actives were present at a ratio of 1:1 than when the actives were present at the 2:1 and 4:1 ratio. In contrast, FIG. 4 illustrates that the composition of Example 46 (mixed fatty acid alkanolamide/pyrrolidone) exhibited thickening at higher water dilution ratios when the actives were present at a high ratios. FIG. 5 illustrates that the composition of Example 50 (mixed fatty acid alkanolamide with dimethyloleylamidopropylamine) exhibited thickening at a wide range of water dilution ratios when the actives were present at a ratio of 4:1.

Example 73

Liquid Hand Soap, Viscosity Increase

Figure 6:
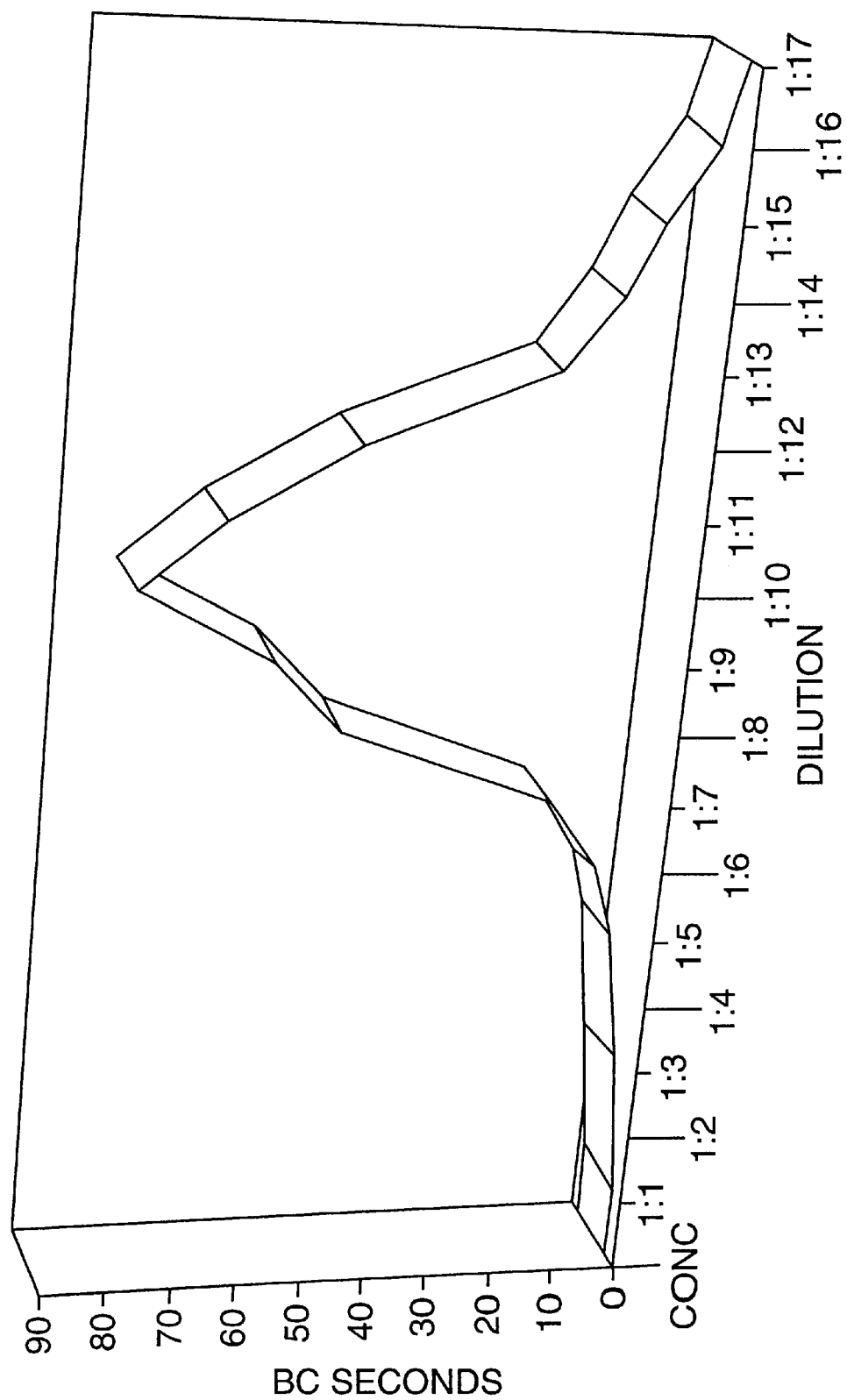

The composition of this example consisted of a mixture of 18 percent oleamidopropyl dimethylamine (available under the trade designation CHEMIDEX O from Chemron corporation, Paso Robles Calif.), 69.485 percent ADMOX LA-1440, 1 percent glacial acetic acid, 5 percent PM ETHER (propylene glycol mono-methyl ether), 5 percent citronellol, 1.5 percent of a fragrance, and 0.015 percent of a red dye (PYLAM LX-10639). This concentrate was diluted to various water dilutions and tested using the Bostwick viscometer in accordance with the above-described test, the results being illustrated in FIG. 6. It can be seen that significant thickening occurred over a wide water dilution range.

Viscosity Comparative Examples

Comparative Example A

For the composition of Comparative Example A, the Example on page 3 of Great Britain patent 1240469 was followed. A composition was mixed consisting of 50 percent of an 85 percent aqueous solution of $H_3PO_4$, 4 percent bis(2-hydroxyethyl)tallow amine oxide (AROMOX T/12, from Akzo Chemie), 0.29 percent lauryl alcohol, and 45.71 percent deionized water. This concentrate composition was immediately tested via the Bostwick viscometer test above-described an exhibited a viscosity of less than 1 second BC, and all subsequent dilutions were also less than 1 second BC. The composition was also made with no water in the sample and the BC viscometer results were the same, except that there was some visual thickening. Another version was made with no water in the sample and with acetic acid replacing the phosphoric acid, and the viscometer test results were the same as when phosphoric acid was used.

Comparative Example B

For the composition of Comparative Example B, 50 percent acetic acid was mixed with 10 percent WITCONATE SXS (an anionic sulfonate), 30 percent AROMOX T/12 (an amine oxide surfactant), and 10 percent deionized water. This concentrate was tested in the above-referenced Bostwick consistometer test. The concentrate had a value of less than one second to travel 20 cm, as well as 1:1 to 1:3 water dilutions. The 1:4 dilution was 4 seconds BC, the 1:5 dilution measured 11 seconds BC, the 1:6 dilution measured 19 seconds BC, the 1:7 dilution measured 11 seconds BC, the 1:8 dilution measured 3 seconds BC, and the 1:9 dilution measured less than 1 second BC.

The composition was also made without the acid. The viscosity testing resulted in the concentrate having a viscosity of less than 1 second BC, and it rapidly thickened on dilution with water to form a gel at 1:4 and 1:5 water dilutions (i.e viscosity of 300 seconds BC or greater), and the composition had a viscosity greater than 1 second BC until a water dilution of 1:19 was reached.

Example 74

Liquid Hand Soap, Cleaning Efficiency

The composition of this example consisted of 7 percent NEROL 800 (a $C_{16}$ alkanol available from Busc Boake Allen Co.), 7 percent AROMOX DM16 (an amine oxide available from Akzo Chemie), 5 percent PM ETHER (propylene glycol mono-methyl ether), 18 percent MACKINE 501 (oleamidopropyl dimethylamine, available from McIntyre Co., 5 percent SANDOPAN DTC ACID LIQUID (a surfactant which helps to lower viscosity), 55.485 percent ADMOX LA-1440, 1 percent glacial acetic acid, 1.5 percent of a fragrance, and 0.015 percent of a red dye (PYLAM LX-10639).

The liquid hand soap composition of Example 74 and three commercially available liquid hand soaps (Comparative Examples C, D and E) were subjected to food grease removal and petroleum grease removal tests, and the results are presented in Table 3. The data in Table 3 clearly show that the composition of Example 74 exhibited a significant cleaning effect.

Various modifications of the invention will be apparent to those skilled in the art. The description and examples herein are merely to be taken as describing and illustrating the invention and are in no way intended to limit the scope of the appended claims.

TABLE 1

| EXAMPLE | AFOC* | AMPHIPHILE |
|---|---|---|
| 1 | ADMOX LA-1440 | SURFADONE LP100 |
| 2 | ADMOX LA-1440 | SURFADONE LP300 |
| 3 | ADMOX LA-1440 | HEXANOL |
| 4 | ADMOX LA-1440 | OCTANOL |
| 5 | ADMOX LA-1440 | MINERAL OIL |
| 6 | ADMOX LA-1440 | CHEMIDEX O |
| 7 | ADMOX LA-1440 | HEXYL ACETATE |
| 8 | ADMOX LA-1440 | LAURIC ACID |
| 9 | ADMOX LA-1440 | EMERY 659 |
| 10 | ADMOX LA-1440 | PELARGONIC ACID |
| 11 | ADMOX LA-1440 | DIISOBUTYLCARBINOL |
| 12 | ALFONfC 810-40 | SURFADONE LP100 |
| 13 | ALFONfC 810-40 | SURFADONE LP300 |
| 14 | ALFONIC 810-40 | HEXANOL |
| 15 | ALFONfC 810-40 | OCTANOL |
| 16 | ALFONIC 810-40 | MINERAL OIL |
| 17 | ALFONIC 810-40 | CHEMIDEX O |
| 18 | ALFONIC 810-40 | HEXYL ACETATE |
| 19 | ALFONIC 810-40 | LAURIC ACID |
| 20 | ALFONIC 810-40 | EMERY 659 |
| 21 | ALFONIC 810-40 | PELARGONIC ACID |
| 22 | ALFONIC 810-40 | DIISOBUTYLCARBINOL |
| 23 | WITCOLATE ES-370 | SURFADONE LP100 |
| 24 | WITCOLATE ES-370 | SURFADONE LP300 |
| 25 | WITCOLATE ES-370 | HEXANOL |
| 26 | WITCOLATE ES-370 | OCTANOL |
| 27 | WITCOLATE ES-370 | MINERAL OIL |
| 28 | WITCOLATE ES-370 | CHEMIDEX O |
| 29 | WITCOLATE ES-370 | HEXYL ACETATE |

TABLE 1-continued

| EXAMPLE | AFOC* | AMPHIPHILE |
|---|---|---|
| 30 | WITCOLATE ES-370 | LAURIC ACID |
| 31 | WITCOLATE ES-370 | EMERY 669 |
| 32 | WITCOLATE ES-370 | PELARGONIC ACID |
| 33 | WITCOLATE ES-370 | DIISOBUTYLCARBINOL |
| 34 | Q-14-2 PG | SURFADONE LP100 |
| 35 | Q-14-2 PG | SURFADONE LP300 |
| 36 | Q-14-2 PG | HEXANOL |
| 37 | Q-14-2 PG | OCTANOL |
| 38 | Q-14-2 PG | MINERAL OIL |
| 39 | Q-14-2 PG | CHEMIDEX O |
| 40 | Q-14-2 PG | HEXYL ACETATE |
| 41 | Q-14-2 PG | LAURIC ACID |
| 42 | Q-14-2 PG | EMERY 659 |
| 43 | Q-14-2 PG | PELARGONIC ACID |
| 44 | Q-14-2 PG | DIISOBUTYLCARBINOL |
| 45 | MONAMID 150ADY | SURFADONE LP100 |
| 46 | MONAMID 150ADY | SURFADONE LP300 |
| 47 | MONAMID 150ADY | HEXANOL |
| 48 | MONAMID 150ADY | OCTANOL |
| 49 | MONAMID 150ADY | MINERAL OIL |
| 50 | MONAMID 150ADY | CHEMIDEX 0 |
| 51 | MONAMID 150ADY | HEXYL ACETATE |
| 52 | MONAMID 150ADY | LAURIC ACID |
| 53 | MONAMID 150ADY | EMERY 659 |
| 54 | MONAMID 150ADY | PELARGONIC ACID |
| 55 | MONAMID 150ADY | DIISOBUTYLCARBINOL |
| 58 | MIRITAINE JC-HA | SURFADONE LP100 |
| 57 | MIRITAINE JC-HA | SURFADONE LP300 |
| 58 | MIRITAINE JC-HA | HEXANOL |
| 59 | MIRITAINE JC-HA | OCTANOL |
| 60 | MIRITAINE JC-HA | MINERAL OIL |
| 61 | MIRITAINE JC-HA | CHEMIDEX O |
| 62 | MIRITAINE JC-HA | HEXYL ACETATE |
| 63 | MIRITAINE JC-HA | LAURIC ACID |
| 64 | MIRITAINE JC-HA | EMERY 659 |
| 65 | MIRITAINE JC-HA | PELARGONIC ACID |
| 66 | MIRITAINE JC-HA | DIISOBUTYLCARBINOL |
| 67 | Q-14-2 PG | DECANOL |
| 68 | MIRITAINE JC-HA | DECANOL |
| 69 | MONAMID 150ADY | DECANOL |
| 70 | WITCOLATE ES-370 | DECANOL |
| 71 | ALFONIC 810-40 | DECANOL |
| 72 | ADMOX LA-1440 | DECANOL |

*AFOC = Aggregate-Forming Organic Compound

TABLE 2

BOSTWICK CONSISTOMETER/20 CM/70F/SECONDS (*=>300 SECONDS)
DILUTION# is ratio of actives AFOC amphiphile
Other dilutions are concentrate:water

| EXAMPLE | DILUTION# | CONC | 1:1 | 1:2 | 1:3 | 1:4 | 1:5 | 1:6 | 1:7 | 1:8 | 1:9 | 1:10 | 1:11 | 1:12 | 1:13 | 1:14 | 1:15 | 1:16 | 1:17 | 1:18 | 1:19 | 1:20 | 1:21 | 1:22 | 1:23 | 1:24 |
|---|---|---|---|---|---|---|---|---|---|---|---|---|---|---|---|---|---|---|---|---|---|---|---|---|---|---|
| 1 | 1:1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 1 | 2:1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 1 | 4:1 | 0 | 10 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 2 | 1:1 | 0 | 0 | 2 | 0 | 2 | 1 | 0 | 0 | 0 | 0 | 0 | 0 | 0 | 0 | 0 | 0 | 0 | 0 | 0 | 0 | 0 | 0 | 0 | 0 | 0 |
| 2 | 2:1 | 0 | 0 | 4 | 0 | 4 | 5 | 3 | 3 | 4 | 5 | 4 | 4 | 4 | 8 | 4 | 2 | 10 | 0 | 0 | 0 | 0 | 0 | 0 | 0 | 0 |
| 2 | 4:1 | 0 | 5 | 0 | 0 | 0 | 57 | 5 | 5 | 4 | 4 | 3 | 2 | 0 | 0 | 0 | 245 | 0 | 6 | 3 | 0 | 0 | 0 | 0 | 0 | 0 |
| 3 | 1:1 | 0 | * | * | * | * | * | * | * | * | * | * | * | * | * | * | * | * | * | * | * | * | * | * | * | * |
| 3 | 2:1 | 0 | 6 | 3 | 3 | 0 | 0 | 0 | 0 | 0 | 0 | 0 | 2 | 7 | 4 | 0 | 0 | 0 | 0 | 0 | 0 | 0 | 0 | 0 | 0 | 0 |
| 3 | 4:1 | 0 | * | * | * | 120 | 184 | * | * | * | * | * | * | * | * | 2 | 290 | 115 | 30 | 6 | 2 | 0 | 0 | 0 | 0 | 0 |
| 4 | 1:1 | 0 | 1 | 1 | 2 | 0 | 0 | 0 | 0 | 0 | 0 | 0 | 0 | 0 | 0 | 0 | 0 | 0 | 0 | 0 | 0 | 0 | 0 | 0 | 0 | 0 |
| 4 | 2:1 | N/S | N/S | | | | | | | | | | | | | | | | | | | | | | | | |
| 4 | 4:1 | N/S | N/S | | | | | | | | | | | | | | | | | | | | | | | | |
| 5 | 1:1 | N/S | N/S | | | | | | | | | | | | | | | | | | | | | | | | |
| 5 | 2:1 | 0 | 3 | 5 | 3 | 5 | 4 | 5 | 0 | 0 | 0 | 0 | 0 | 0 | 0 | 0 | 0 | 0 | 0 | 0 | 0 | 0 | 0 | 0 | 0 | 0 |
| 5 | 4:1 | 0 | 9 | 10 | 10 | 6 | 9 | 7 | 0 | 0 | 0 | 0 | 0 | 0 | 0 | 0 | 0 | 0 | 0 | 0 | 0 | 0 | 0 | 0 | 0 | 0 |
| 6 | 1:1 | 0 | 0 | 1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 6 | 2:1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 6 | 4:1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 7 | 1:1 | 0 | | | | | | | | | | | | | | | | | | | | | | | | | |
| 7 | 2:1 | 0 | | | | | | | | | | | | | | | | | | | | | | | | | |
| 7 | 4:1 | SOL | | | | | | | | | | | | | | | | | | | | | | | | | |
| 8 | 1:1 | N/S | N/S | | | | | | | | | | | | | | | | | | | | | | | | |
| 8 | 2:1 | N/S | N/S | | | | | | | | | | | | | | | | | | | | | | | | |
| 8 | 4:1 | N/S | N/S | | | | | | | | | | | | | | | | | | | | | | | | |
| 9 | 1:1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 9 | 2:1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 9 | 4:1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 10 | 1:1 | N/S | N/S | | | | | | | | | | | | | | | | | | | | | | | | |
| 10 | 2:1 | N/S | N/S | | | | | | | | | | | | | | | | | | | | | | | | |
| 10 | 4:1 | N/S | N/S | | | | | | | | | | | | | | | | | | | | | | | | |
| 11 | 1:1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 11 | 2:1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 11 | 4:1 | 0 | 0 | | | | | | | | | | | | | | | | | | | | | | | | |
| 12 | 1:1 | N/S | N/S | | | | | | | | | | | | | | | | | | | | | | | | |
| 12 | 2:1 | N/S | N/S | | | | | | | | | | | | | | | | | | | | | | | | |
| 13 | 1:1 | 0 | 148 | N/S | | | | | | | | | | | | | | | | | | | | | | | |
| 13 | 2:1 | 0 | N/S | N/S | | | | | | | | | | | | | | | | | | | | | | | |
| 13 | 4:1 | 0 | 9 | | | | | | | | | | | | | | | | | | | | | | | | |
| 14 | 1:1 | 0 | 84 | | | | | | | | | | | | | | | | | | | | | | | | |
| 14 | 2:1 | 0 | N/S | | | | | | | | | | | | | | | | | | | | | | | | |
| 14 | 4:1 | 0 | N/S | | | | | | | | | | | | | | | | | | | | | | | | |
| 15 | 1:1 | 0 | N/S | | | | | | | | | | | | | | | | | | | | | | | | |
| 15 | 2:1 | 0 | N/S | | | | | | | | | | | | | | | | | | | | | | | | |
| 15 | 4:1 | 0 | N/S | | | | | | | | | | | | | | | | | | | | | | | | |

TABLE 2-continued

BOSTWICK CONSISTOMETER/20 CM/70F/SECONDS (*=>300 SECONDS)
DILUTION# is ratio of actives AFOC amphiphlle
Other dilutions are concentrate:water

| EXAMPLE | DILUTION# | CONC | 1:1 | 1:2 | 1:3 | 1:4 | 1:5 | 1:6 | 1:7 | 1:8 | 1:9 | 1:10 | 1:11 | 1:12 | 1:13 | 1:14 | 1:15 | 1:16 | 1:17 | 1:18 | 1:19 | 1:20 | 1:21 | 1:22 | 1:23 | 1:24 |
|---|---|---|---|---|---|---|---|---|---|---|---|---|---|---|---|---|---|---|---|---|---|---|---|---|---|---|
| 16 | 1:1 | 0 | N/S | | | | | | | | | | | | | | | | | | | | | | | |
| 16 | 2:1 | 0 | N/S | | | | | | | | | | | | | | | | | | | | | | | |
| 16 | 4:1 | 0 | N/S | | | | | | | | | | | | | | | | | | | | | | | |
| 17 | 1:1 | 0 | * | N/S | | | | | | | | | | | | | | | | | | | | | | |
| 17 | 2:1 | 0 | 18 | 6 | | | | | | | | | | | | | | | | | | | | | | |
| 17 | 4:1 | 0 | * | 60 | | | | | | | | | | | | | | | | | | | | | | |
| 18 | 1:1 | 0 | N/S | | | | | | | | | | | | | | | | | | | | | | | |
| 18 | 2:1 | 0 | N/S | | | | | | | | | | | | | | | | | | | | | | | |
| 18 | 4:1 | 0 | N/S | | | | | | | | | | | | | | | | | | | | | | | |
| 19 | 1:1 | N/S | | | | | | | | | | | | | | | | | | | | | | | | |
| 19 | 2:1 | N/S | | | | | | | | | | | | | | | | | | | | | | | | |
| 19 | 4:1 | N/S | | | | | | | | | | | | | | | | | | | | | | | | |
| 20 | 1:1 | 0 | N/S | | | | | | | | | | | | | | | | | | | | | | | |
| 20 | 2:1 | 0 | N/S | | | | | | | | | | | | | | | | | | | | | | | |
| 20 | 4:1 | 0 | N/S | | | | | | | | | | | | | | | | | | | | | | | |
| 21 | 1:1 | 0 | N/S | | | | | | | | | | | | | | | | | | | | | | | |
| 21 | 2:1 | 0 | N/S | | | | | | | | | | | | | | | | | | | | | | | |
| 21 | 4:1 | 0 | N/S | | | | | | | | | | | | | | | | | | | | | | | |
| 22 | 1:1 | 0 | N/S | | | | | | | | | | | | | | | | | | | | | | | |
| 22 | 2:1 | 0 | N/S | | | | | | | | | | | | | | | | | | | | | | | |
| 22 | 4:1 | 0 | N/S | | | | | | | | | | | | | | | | | | | | | | | |
| 23 | 1:1 | 0 | 0 | | | | | | | | | | | | | | | | | | | | | | | |
| 23 | 2:1 | * | | | | | | | | | | | | | | | | | | | | | | | | |
| 23 | 4:1 | * | | | | | | | | | | | | | | | | | | | | | | | | |
| 24 | 1:1 | 48 | * | 103 | * | 145 | * | * | * | * | * | * | 14 | 3 | 0 | 0 | 0 | 0 | 0 | 0 | 0 | 0 | 0 | 0 | 0 | 0 |
| 24 | 2:1 | * | * | * | * | N/S | | | | | | | | | | | | | | | | | | | | |
| 24 | 4:1 | * | N/S | | | | | | | | | | | | | | | | | | | | | | | |
| 25 | 1:1 | 0 | * | * | * | 30 | 4 | 0 | 0 | 0 | 0 | 0 | 0 | 0 | 0 | 0 | 0 | 0 | 0 | 0 | 0 | 0 | 0 | 0 | 0 | 0 |
| 25 | 2:1 | 0 | * | N/S | | | | | | | | | | | | | | | | | | | | | | |
| 25 | 4:1 | * | * | N/S | | | | | | | | | | | | | | | | | | | | | | |
| 26 | 1:1 | 0 | * | 78 | 94 | 0 | 0 | 0 | 0 | 0 | * | 300 | 80 | 0 | 0 | 0 | 0 | 0 | 0 | 0 | 0 | 0 | 0 | 0 | 0 | 0 |
| 26 | 2:1 | 0 | * | * | 6 | 0 | 0 | 0 | 0 | 0 | 0 | 0 | 0 | 0 | 0 | 0 | 0 | 0 | 0 | 0 | 0 | 0 | 0 | 0 | 0 | 0 |
| 26 | 4:1 | 0 | * | | | | | | | | | | | | | | | | | | | | | | | | |
| 27 | 1:1 | * | N/S | | | | | | | | | | | | | | | | | | | | | | | |
| 27 | 2:1 | * | N/S | | | | | | | | | | | | | | | | | | | | | | | |
| 27 | 4:1 | * | N/S | | | | | | | | | | | | | | | | | | | | | | | |
| 28 | 1:1 | N/S | | | | | | | | | | | | | | | | | | | | | | | | |
| 28 | 2:1 | * | * | N/S | | | | | | | | | | | | | | | | | | | | | | |
| 28 | 4:1 | * | * | N/S | | | | | | | | | | | | | | | | | | | | | | |
| 29 | 1:1 | N/S | | | | | | | | | | | | | | | | | | | | | | | | |
| 29 | 2:1 | N/S | | | | | | | | | | | | | | | | | | | | | | | | |
| 29 | 4:1 | N/S | | | | | | | | | | | | | | | | | | | | | | | | |
| 30 | 1:1 | SOL | | | | | | | | | | | | | | | | | | | | | | | | |
| 30 | 2:1 | N/S | | | | | | | | | | | | | | | | | | | | | | | | |
| 30 | 4:1 | N/S | | | | | | | | | | | | | | | | | | | | | | | | |
| 31 | 1:1 | SOL | | | | | | | | | | | | | | | | | | | | | | | | |

TABLE 2-continued

BOSTWICK CONSISTOMETER/20 CM/70F/SECONDS (*=>300 SECONDS)
DILUTION# is ratio of acitves AFOC amphiphlle
Other dilutions are concentrate:water

| EXAMPLE | DILUTION# | CONC | 1:1 | 1:2 | 1:3 | 1:4 | 1:5 | 1:6 | 1:7 | 1:8 | 1:9 | 1:10 | 1:11 | 1:12 | 1:13 | 1:14 | 1:15 | 1:16 | 1:17 | 1:18 | 1:19 | 1:20 | 1:21 | 1:22 | 1:23 | 1:24 |
|---|---|---|---|---|---|---|---|---|---|---|---|---|---|---|---|---|---|---|---|---|---|---|---|---|---|---|
| 31 | 2:1 | N/S | | | | | | | | | | | | | | | | | | | | | | | | |
| 31 | 4:1 | N/S | | | | | | | | | | | | | | | | | | | | | | | | |
| 32 | 1:1 | N/S | | | | | | | | | | | | | | | | | | | | | | | | |
| 32 | 2:1 | N/S | | | | | | | | | | | | | | | | | | | | | | | | |
| 32 | 4:1 | N/S | | | | | | | | | | | | | | | | | | | | | | | | |
| 33 | 1:1 | N/S | | | | | | | | | | | | | | | | | | | | | | | | |
| 33 | 2:1 | N/S | | | | | | | | | | | | | | | | | | | | | | | | |
| 33 | 4:1 | N/S | | | | | | | | | | | | | | | | | | | | | | | | |
| 34 | 1:1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 34 | 2:1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 34 | 4:1 | 0 | 0 | 2 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 35 | 1:1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 35 | 2:1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 35 | 4:1 | 0 | 0 | 64 | 215 | * | * | * | * | * | * | * | * | * | * | * | * | 0 | 0 | 0 | 0 | 0 | 0 | 0 | 0 | 0 | 0 |
| 36 | 1:1 | 0 | 3 | N/S | | | | | | | | | | | | | | | | | | | | | | |
| 36 | 2:1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 36 | 4:1 | 0 | 185 | * | * | * | * | * | * | * | * | * | 84 | * | * | 160 | 15 | 1 | 0 | 0 | 0 | 0 | 0 | 0 | 0 | 0 |
| 37 | 1:1 | 0 | 239 | * | 43 | 0 | 0 | 0 | 0 | 0 | 0 | 0 | 0 | 0 | 0 | 0 | 0 | 0 | 0 | 0 | 0 | 0 | 0 | 0 | 0 | 0 |
| 37 | 2:1 | 0 | 3 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 37 | 4:1 | 0 | | | | | | | | | | | | | | | | | | | | | | | | |
| 38 | 1:1 | N/S | | | | | | | | | | | | | | | | | | | | | | | | |
| 38 | 2:1 | N/S | | | | | | | | | | | | | | | | | | | | | | | | |
| 38 | 4:1 | N/S | | | | | | | | | | | | | | | | | | | | | | | | |
| 39 | 1:1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 39 | 2:1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 39 | 4:1 | 0 | N/S | | | | | | | | | | | | | | | | | | | | | | | | |
| 40 | 1:1 | 0 | 0 | 0 | 0 | | | | | | | | | | | | | | | | | | | | | |
| 40 | 2:1 | 0 | 0 | N/S | | | | | | | | | | | | | | | | | | | | | | |
| 40 | 4:1 | 0 | 0 | | | | | | | | | | | | | | | | | | | | | | | | |
| 41 | 1:1 | N/S | | | | | | | | | | | | | | | | | | | | | | | | |
| 41 | 2:1 | N/S | | | | | | | | | | | | | | | | | | | | | | | | |
| 41 | 4:1 | N/S | | | | | | | | | | | | | | | | | | | | | | | | |
| 42 | 1:1 | N/S | | | | | | | | | | | | | | | | | | | | | | | | |
| 42 | 2:1 | N/S | | | | | | | | | | | | | | | | | | | | | | | | |
| 42 | 4:1 | N/S | | | | | | | | | | | | | | | | | | | | | | | | |
| 43 | 1:1 | 0 | * | * | * | * | * | * | * | * | * | * | * | 160 | * | 15 | 1 | 0 | 0 | 0 | 0 | 0 | 0 | 0 | 0 | 0 |
| 43 | 2:1 | 0 | 7 | 13 | 0 | N/S | | | | | | | | | | | | | | | | | | | | |
| 43 | 4:1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 44 | 1:1 | N/S | | | | | | | | | | | | | | | | | | | | | | | | |
| 44 | 2:1 | N/S | | | | | | | | | | | | | | | | | | | | | | | | |
| 44 | 4:1 | 0 | 0 | | | | | | | | | | | | | | | | | | | | | | | | |
| 45 | 1:1 | N/S | | | | | | | | | | | | | | | | | | | | | | | | |
| 45 | 2:1 | 0 | 40 | 0 | 0 | 0 | 0 | 0 | 0 | 240 | 20 | 7 | 4 | 2 | 0 | 0 | 0 | 0 | 0 | 0 | 0 | 0 | 0 | 0 | 0 | 0 |
| 45 | 4:1 | 0 | 140 | 29 | 50 | * | * | * | * | * | * | * | * | * | 0 | 0 | 0 | 0 | 0 | 0 | 0 | 0 | 0 | 0 | 0 | 0 |
| 46 | 1:1 | N/S | | | | | | | | | | | | | | | | | | | | | | | | |
| 46 | 2:1 | 0 | 230 | 1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

TABLE 2-continued

BOSTWICK CONSISTOMETER/20 CM/70F/SECONDS (*=>300 SECONDS)
DILUTION# is ratio of actives AFOC amphiphlle
Other dilutions are concentrate:water

| EXAMPLE | DILUTION# | CONC | 1:1 | 1:2 | 1:3 | 1:4 | 1:5 | 1:6 | 1:7 | 1:8 | 1:9 | 1:10 | 1:11 | 1:12 | 1:13 | 1:14 | 1:15 | 1:16 | 1:17 | 1:18 | 1:19 | 1:20 | 1:21 | 1:22 | 1:23 | 1:24 |
|---|---|---|---|---|---|---|---|---|---|---|---|---|---|---|---|---|---|---|---|---|---|---|---|---|---|---|
| 46 | 4:1 | 0 | * | * | * | * | * | * | * | * | * | * | 150 | 125 | 25 | 6 | 0 | 0 | 0 | 0 | 0 | 0 | 0 | 0 | 0 | 0 |
| 47 | 1:1 | 0 | N/S | | | | | | | | | | | | | | | | | | | | | | | |
| 47 | 2:1 | 0 | N/S | | | | | | | | | | | | | | | | | | | | | | | |
| 47 | 4:1 | 0 | 0 | 0 | | | | | | | | | | | | | | | | | | | | | | |
| 48 | 1:1 | 0 | N/S | | | | | | | | | | | | | | | | | | | | | | | |
| 48 | 2:1 | 0 | N/S | | | | | | | | | | | | | | | | | | | | | | | |
| 48 | 4:1 | 0 | SOL | | | | | | | | | | | | | | | | | | | | | | | |
| 49 | 1:1 | 0 | * | * | * | * | * | * | N/S | | | | | | | | | | | | | | | | | |
| 49 | 2:1 | 0 | * | * | * | 272 | 153 | 50 | 62 | 61 | | | | | | | | | | | | | | | | |
| 49 | 4:1 | 0 | * | 167 | 173 | 186 | * | * | * | * | | | | | | | | | | | | | | | | |
| 50 | 1:1 | 0 | * | 56 | 16 | 2 | 0 | 0 | 0 | 0 | 10 | | | | | | | | | | | | | | | |
| 50 | 2:1 | 0 | * | * | * | * | * | * | * | * | * | * | | | | | | | | | | | | | | |
| 50 | 4:1 | 0 | * | * | * | * | * | * | * | * | * | * | * | * | * | * | * | * | 240 | 150 | 73 | 55 | 37 | 17 | 4 | 0 |
| 51 | 1:1 | 0 | N/S | | | | | | | | | | | | | | | | | | | | | | | |
| 51 | 2:1 | 0 | N/S | | | | | | | | | | | | | | | | | | | | | | | |
| 51 | 4:1 | 0 | N/S | | | | | | | | | | | | | | | | | | | | | | | |
| 52 | 1:1 | SOL | | | | | | | | | | | | | | | | | | | | | | | | |
| 52 | 2:1 | N/S | | | | | | | | | | | | | | | | | | | | | | | | |
| 52 | 4:1 | N/S | | | | | | | | | | | | | | | | | | | | | | | | |
| 53 | 1:1 | 0 | * | * | N/S | | | | | | | | | | | | | | | | | | | | | |
| 53 | 2:1 | N/S | | | | | | | | | | | | | | | | | | | | | | | | |
| 53 | 4:1 | N/S | | | | | | | | | | | | | | | | | | | | | | | | |
| 54 | 1:1 | 0 | N/S | | | | | | | | | | | | | | | | | | | | | | | |
| 54 | 2:1 | 0 | N/S | | | | | | | | | | | | | | | | | | | | | | | |
| 54 | 4:1 | 0 | * | * | * | * | 35 | 18 | 0 | 0 | 0 | 0 | 0 | 0 | 0 | | | | | | | | | | | |
| 55 | 1:1 | 0 | N/S | | | | | | | | | | | | | | | | | | | | | | | |
| 55 | 2:1 | 0 | N/S | | | | | | | | | | | | | | | | | | | | | | | |
| 55 | 4:1 | 0 | N/S | | | | | | | | | | | | | | | | | | | | | | | |
| 56 | 1:1 | 0 | 0 | 0 | 0 | 0 | 0 | 0 | 0 | 0 | 0 | 0 | 0 | 0 | 0 | 0 | | | | | | | | | | |
| 56 | 2:1 | 0 | 0 | 0 | 0 | 0 | 0 | 0 | 0 | 0 | 0 | 0 | 0 | 0 | 0 | 0 | | | | | | | | | | |
| 56 | 4:1 | 0 | 0 | 0 | 0 | 0 | 0 | 0 | 0 | 0 | 0 | 0 | 0 | 0 | 0 | 0 | | | | | | | | | | |
| 57 | 1:1 | 0 | 0 | 0 | 0 | 0 | 0 | 0 | 0 | 0 | 0 | 0 | 0 | 0 | 0 | 0 | | | | | | | | | | |
| 57 | 2:1 | 0 | 0 | 0 | 0 | 0 | 0 | 0 | 0 | 0 | 0 | 0 | 0 | 0 | 0 | 0 | | | | | | | | | | |
| 57 | 4:1 | 0 | | | | | | | | | | | | | | | | | | | | | | | | |
| 58 | 1:1 | N/S | | | | | | | | | | | | | | | | | | | | | | | | |
| 58 | 2:1 | N/S | | | | | | | | | | | | | | | | | | | | | | | | |
| 58 | 4:1 | N/S | | | | | | | | | | | | | | | | | | | | | | | | |
| 59 | 1:1 | * | | | | | | | | | | | | | | | | | | | | | | | | |
| 59 | 2:1 | * | | | | | | | | | | | | | | | | | | | | | | | | |
| 59 | 4:1 | 0 | 0 | | | | | | | | | | | | | | | | | | | | | | | |
| 60 | 1:1 | N/S | | | | | | | | | | | | | | | | | | | | | | | | |
| 60 | 2:1 | N/S | | | | | | | | | | | | | | | | | | | | | | | | |
| 60 | 4:1 | N/S | | | | | | | | | | | | | | | | | | | | | | | | |
| 61 | 1:1 | 0 | 5 | 3 | 3 | 2 | 0 | 0 | 0 | 0 | 0 | 0 | 0 | 0 | 0 | 0 | | | | | | | | | | |
| 61 | 2:1 | 0 | 0 | 0 | 0 | 0 | 0 | 0 | 0 | 0 | 0 | 0 | 0 | 0 | 0 | 0 | | | | | | | | | | |
| 61 | 4:1 | 0 | 0 | 0 | 0 | 0 | 0 | 0 | 0 | 0 | 0 | 0 | 0 | 0 | 0 | 0 | | | | | | | | | | |

TABLE 2-continued

BOSTWICK CONSISTOMETER/20 CM/70F/SECONDS (*=>300 SECONDS)
DILUTION# is ratio of acitves AFOC amphiphlle
Other dilutions are concentrate:water

| EXAMPLE | DILUTION# | CONC | 1:1 | 1:2 | 1:3 | 1:4 | 1:5 | 1:6 | 1:7 | 1:8 | 1:9 | 1:10 | 1:11 | 1:12 | 1:13 | 1:14 | 1:15 | 1:16 | 1:17 | 1:18 | 1:19 | 1:20 | 1:21 | 1:22 | 1:23 | 1:24 |
|---|---|---|---|---|---|---|---|---|---|---|---|---|---|---|---|---|---|---|---|---|---|---|---|---|---|---|
| 62 | 1:1 | N/S | | | | | | | | | | | | | | | | | | | | | | | | |
| 62 | 2:1 | N/S | | | | | | | | | | | | | | | | | | | | | | | | |
| 62 | 4:1 | N/S | | | | | | | | | | | | | | | | | | | | | | | | |
| 63 | 1:1 | * | N/S | | | | | | | | | | | | | | | | | | | | | | | |
| 63 | 2:1 | 0 | 0 | 0 | 0 | 0 | 0 | 0 | 0 | 0 | 0 | 0 | 0 | 0 | 0 | 0 | | | | | | | | | | |
| 63 | 4:1 | 0 | 0 | 0 | 0 | 0 | 0 | 0 | 0 | 0 | 0 | 0 | 0 | 0 | 0 | 0 | | | | | | | | | | |
| 64 | 1:1 | * | N/S | | | | | | | | | | | | | | | | | | | | | | | |
| 64 | 2:1 | N/S | | | | | | | | | | | | | | | | | | | | | | | | |
| 64 | 4:1 | N/S | | | | | | | | | | | | | | | | | | | | | | | | |
| 65 | 1:1 | * | N/S | | | | | | | | | | | | | | | | | | | | | | | |
| 65 | 2:1 | 0 | 0 | 0 | 0 | 0 | 0 | 0 | 0 | 0 | 0 | 0 | 0 | 0 | 0 | | | | | | | | | | | |
| 65 | 4:1 | 0 | 0 | 0 | 0 | 0 | 0 | 0 | 0 | 0 | 0 | 0 | 0 | 0 | 0 | | | | | | | | | | | |
| 66 | 1:1 | N/S | | | | | | | | | | | | | | | | | | | | | | | | |
| 66 | 2:1 | N/S | | | | | | | | | | | | | | | | | | | | | | | | |
| 66 | 4:1 | N/S | | | | | | | | | | | | | | | | | | | | | | | | |
| 67 | 1:1 | 0 | * | * | * | * | * | * | * | * | * | * | * | * | * | | | | | | | | | | | |
| 67 | 2:1 | 0 | 0 | 1 | 0 | 0 | 0 | 0 | 0 | 0 | 0 | 0 | 0 | 0 | 0 | | | | | | | | | | | |
| 67 | 4:1 | 0 | 0 | 0 | 0 | 0 | 0 | 0 | 0 | 0 | 0 | 0 | 0 | 0 | 0 | | | | | | | | | | | |
| 68 | 1:1 | N/S | | | | | | | | | | | | | | | | | | | | | | | | |
| 68 | 2:1 | N/S | | | | | | | | | | | | | | | | | | | | | | | | |
| 68 | 4:1 | 0 | 0 | 0 | 0 | 0 | 0 | 0 | 0 | 0 | 0 | 0 | 0 | 0 | 245 | | | | | | | | | | | |
| 69 | 1:1 | 0 | 0 | | | | | | | | | | | | | 0 | | | | | | | | | | |
| 69 | 2:1 | 0 | N/S | | | | | | | | | | | | | | | | | | | | | | | |
| 69 | 4:1 | 0 | N/S | | | | | | | | | | | | | | | | | | | | | | | |

TABLE 3

Food Grease and Petroleum Grease Percent Removal

| Example[1] | Test | 1 MIN | 2 MIN | 3 MIN | 4 MIN | 5 MIN |
|---|---|---|---|---|---|---|
| 74 | Petroleum | 20 | 50 | 70 | 80 | 90 |
|  | Food | 97 | 100 | — | — | — |
| C | Petroleum | 10 | 30 | 40 | 50 | 50 |
|  | Food | 30 | 60 | 80 | 100 | — |
| D | Petroleum | 15 | 25 | 45 | 55 | 60 |
|  | Food | 80 | 95 | 97 | 100 | — |
| E | Petroleum | 40 | 70 | 80 | 95 | 100 |
|  | Food | 90 | 95 | 100 | — | — |

[1]Comparative Example C was the liquid hand soap known under the trade designation ENHANCE LOTION SOAP, from S.C. Johnson & Son, Racine, Wisconsin.
Comparative Example D was the liquid hand soap known under the trade designation EPICARE LOTION SOAP, from Ecolab Company, St. Paul Minnesota.
Comparative Example E is the liquid hand soap known under the trade designation SANIFRESH GENTLE LOTION SOAP, from Scott Paper Company.

What is claimed is:

1. A concentrated cleaning composition which readily increases in viscosity upon dilution with water, the concentrated cleaning composition comprising:

A) an aggregate-forming organic compound;
B) a nonaggregating or mildly aggregating organic compound; the aggregate-forming compound and the nonaggregating or mildly aggregating organic compound providing a viscosity of less than 1 second BC, the composition being readily dilutable without significant shearing, and adapted to have a viscosity of at least about 5 seconds BC at a weight ratio of water to the composition of 8:1 and greater without the addition of desolubilizers, additional surfactants, hydrophobically modified polymers, or a combination thereof, wherein:
  (i) the aggregate-forming organic compound is quaternary amine salts; and
  (ii) the nonaggregating or mildly aggregating organic compound is selected from the group consisting of octanoic acid, nonanoic acid and lauric acid,
said quaternary amine salt and said nonaggregating organic compound present at a weight ratio of quaternary amine salt to nonaggregating organic compound within the range from about 1:1 to about 5:1.

2. Composition in accordance with claim 1 wherein said quaternary amine salt has the general formula (II):

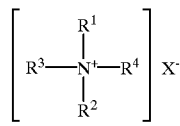

(II)

wherein $R^1$ and $R^2$ are the same or different and are selected from the group consisting of alkyl and substituted alkyl groups, $R^3$ is selected from the group consisting of straight chain alkyls having from about 10 to 20 carbon atoms, branched chain alkyls having from about 10 to 20 carbon atoms, straight chain heteroalkyls having from about 10 to 20 carbon atoms, and branched chain heteroalkyls having from about 10 to 20 carbon atoms, $R^4$ is selected from the group consisting of alkyl groups having from 1 to about 5 carbon atoms, and X is a halogen atom.

3. Composition in accordance with claim 2 wherein said quaternary amine salt is isodecyloxypropyldihydroxyethylmethyl ammonium chloride.

4. Composition in accordance with claim 1 further including a water soluble glycol ether selected from the group consisting of ethylene glycol methyl ether, ethylene glycol ethyl ether, ethylene glycol mono-n-butyl ether, diethylene glycol methyl ether, diethylene glycol ethyl ether, methoxy triglycol, ethoxy triglycol, butoxy triglycol, 1-butoxyethoxy-2-propanol, propylene glycol n-propyl ether, propylene glycol methyl ether, dipropylene glycol methyl ether, 3-methyl-3-methoxybutanol and propylene glycol mono-t-butyl ether, the weight ratio of said aggregate forming compound to said water soluble glycol being within the range from about 1:1 to about 20:1.

5. A concentrated cleaning composition comprising:

a quaternary amine salt within the general formula (II):

(II)

wherein $R^1$ and $R^2$ are the same or different and are selected from the group consisting of alkyl and substituted alkyl groups, $R^3$ is selected from the group consisting of straight chain alkyls having from about 10 to 20 carbon atoms, branched chain alkyls having from about 10 to 20 carbon atoms, straight chain heteroalkyls having from about 10 to 20 carbon atoms, and branched chain heteroalkyls having from about 10 to 20 carbon atoms, $R^4$ is selected from the group consisting of alkyl groups having from 1 to about 5 carbon atoms, and X is a halogen atom; and a non-aggregating or mildly aggregating compound having a water solubility of less than 1% by weight at 20°, said quaternary amine salt and said nonaggregating organic compound present at a weight ratio of quaternary amine salt to nonaggregating organic compound within the range from about 1:1 to about 5:1, said non-aggregating or mildly aggregating compound selected from the group consisting of octanoic acid, nonanoic acid, and lauric acid;

said quaternary amine salt and said non-aggregating or mildly aggregating compound providing a viscosity of less than 1 second BC, the composition being readily dilutable without significant shearing, and adapted to have a viscosity of at least 5 seconds BC at a weight ratio of water to the composition of 8:1 and greater without the addition of desolubizers, additional surfactants, hydrophobically modified polymers, or a combination thereof.

6. The concentrated cleaning composition as defined in claim 5 wherein said quaternary amine salt is isodecyloxypropyldihydroxyethylmethyl ammonium chloride.

7. A concentrated cleaning composition which readily increases in viscosity upon dilution with water, the concentrated cleaning composition comprising:

a) a noncyclic alkanolamide aggregate-forming organic compound, and
b) a nonaggregating or mildly aggregating mineral oil, wherein the noncyclic alkanolamide aggregate-forming organic compound and the nonaggregating or mildly aggregating mineral oil are present in a weight ratio of alkanolamide to nonaggregrating or mildly aggregating organic compound within the range from about 1:1 to about 6:1 to provide a viscosity of less than 1 second BC, the composition being readily dilutable without significant shearing, and adapted to have a viscosity of at least about 5 seconds BC at a weight ratio of water to the composition of 8:1 and greater without the addition of desolubilizers, additional surfactants, hydrophobically modified polymers, or a combination thereof.

* * * * *

UNITED STATES PATENT AND TRADEMARK OFFICE
CERTIFICATE OF CORRECTION

PATENT NO.   : 6,150,320
DATED        : November 21, 2000
INVENTOR(S)  : James A. McDonell and Jerry W. Mlinar It is certified that error appears in the above-identified patent and that said Letters Patent is hereby corrected as shown below:

<u>Title page,</u>
Item [56], References Cited, under U.S. PATENT DOCUMENTS, please insert
-- 4,472,291     9/1984        Rosano        252/186.28 --.

<u>Column 8,</u>
Line 66, delete "Rio" and insert in place thereof -- $R_{10}$ --.

<u>Column 17,</u>
Lines 29, 30 and 32, delete "ALFONfC" and insert in place thereof -- ALFONIC --.

<u>Column 18,</u>
Line 6, delete "EMERY 669" and insert in place thereof -- EMERY 659 --.

<u>Table 2,</u>
Under the second Example 6 under the heading "1:4" delete "6" and insert in place thereof -- 8 --.
Under the second Example 46 under the heading "1:2" delete "1" and insert in place thereof -- 4 --.
Under the third Example 49 under the heading "1:4" delete "186" and insert in place thereof -- 188 --.

Signed and Sealed this

Twenty-seventh Day of August, 2002

*Attest:*

JAMES E. ROGAN
*Attesting Officer*   *Director of the United States Patent and Trademark Office*